(12) United States Patent
Anderson

(10) Patent No.: US 6,524,861 B1
(45) Date of Patent: Feb. 25, 2003

(54) BLOOD COAGULATION ANALYZER

(75) Inventor: Eric S. Anderson, Pleasantville, NY (US)

(73) Assignee: Medical Laboratory Automation, Inc., Lexington, MA (US)

(*) Notice: Subject to any disclaimer, the term of this patent is extended or adjusted under 35 U.S.C. 154(b) by 0 days.

(21) Appl. No.: 09/235,530

(22) Filed: Jan. 22, 1999

(51) Int. Cl.[7] .......................... G01N 33/86; G06F 19/00

(52) U.S. Cl. ............................. 436/69; 436/43; 436/47; 436/48; 436/50; 436/55; 422/63; 422/65; 422/67; 422/73; 702/19; 702/21

(58) Field of Search ........................... 436/69, 43, 47, 436/48, 50, 55; 422/63, 65, 67, 73; 702/19, 21

(56) References Cited

U.S. PATENT DOCUMENTS

| | | | | |
|---|---|---|---|---|
| 4,047,890 A | * | 9/1977 | Eichelberger et al. | 23/230 |
| 4,720,787 A | | 1/1988 | Lipscomb | 364/416 |
| 5,169,786 A | | 12/1992 | Carroll et al. | 436/69 |
| 5,629,707 A | | 5/1997 | Heuvel et al. | 342/357 |
| 5,646,046 A | | 7/1997 | Fischer et al. | 436/49 |

FOREIGN PATENT DOCUMENTS

| | | | |
|---|---|---|---|
| EP | 0 062 616 A1 | 10/1982 | G01N/33/86 |
| EP | 0 304 283 A2 | 2/1989 | G01N/11/00 |

OTHER PUBLICATIONS

P. Deuflhard et al., "4. Larkin—A Software Package for the Numerical Simulation of LARge Arising in Chemical Reaction KINetics," Springer Ser. Chem. Phys., vol. 18, pp. 38–55, 1981.

R.F. Doolittle, "Fibrinogen & Fibrin," Scientific American, vol. 245, No. 6, pp. 126–135, Dec. 1981.

J.W. Weisel et al., "Computer Modeling of Fibrin Polymerization on Kinetics Correlated With . . . ," Biophysical Journal, vol. 63, pp. 111–128, Jul. 1992.

(List continued on next page.)

Primary Examiner—Jill Warden
Assistant Examiner—Monique T. Cole
(74) Attorney, Agent, or Firm—Wolf, Greenfield & Sacks, P.C.

(57) ABSTRACT

One method and apparatus for analyzing clotting characteristics of a blood sample includes the use of a non-linear equation having coefficients capable of being related to the underlying clotting processes. The non-linear equation is curve fit to a waveform of a clotting sample to provide values for the coefficients of the non-linear function. Once the coefficients are obtained, an inference engine may be used to evaluate the non-linear relationship between the coefficients and factor concentrations within the blood sample. Advantageously, the waveform of the actual sample may be detrended to extract a residual oscillatory component to aid in the determination of initial coefficients for simplifying the curve fit operation. The non-linear equation may additionally be used for providing simulated clotting waveforms for testing clot analysis instruments. A residual oscillatory component may advantageously be extracted from the clotting signal. The oscillatory components may be used to provide a high quality clot time indicator for the sample. In addition, the oscillatory component may be used to correct for clot anomalies by correlating the frequency of the oscillatory to various physical characteristics of the blood clot. The oscillatory component may be used to provide initial estimates for values of the coefficients of the logistic. The logistic, because it represents knowledge as to the underlying chemistry of the clotting process, may also be used to provide initial estimates for coefficients of the logistic, and may also be used to enhance the accuracy of existing polynomial template clot analysis techniques. The logistic model may also be used to verify the operation of clot analysis tools.

43 Claims, 14 Drawing Sheets

OTHER PUBLICATIONS

T.B. Givens et al., "Interpretation of Clot Formation Parameters from APTT and PT Assays Using Neural Networks," Clinical Chemistry, vol. 42, Jul. 1996.

T.B. Givens et al., "Predicting the Presence of Plasma Heparin Using Neural Networks . . . ," Comp. Biol., Med., vol. 26, No. 6, pp. 463–476, 1996.

B. Pohl et al., "The Quick Machine—A Mathematical Model for the Extrinsic Activation of Coagulation," Haemostasis, vol. 24, pp. 325–337, 1994.

M.E. Nesheim et al., "'Clotspeed,' A Mathematical Simulation of the Functional Properties of Prothrombinase," Journal of Biological Chemistry, vol. 259, No. 3, pp. 1447–1453, Feb. 10, 1984.

D.M. Cocchetto et al., "Simulation: An Underutilized Approach to Coagulation System Model Evaluation," Thrombosis Research, vol. 28, pp. 223–236, 1982.

U. Larsson et al., "Fibrinogen and the Early Stages of Polymerization . . . ," Biochimica et Biophysica Acta, vol. 915, pp. 172–179, 1987.

P. Baumann et al., "Simulation of the Extrinsic Pathway of the Plasmatic Clotting System," Haemostasis, vol. 21, pp. 329–337, 1991.

P. Baumann et al., "Computerized Analysis of the in vitro Activation of the Plasmatic Clotting System," Haemostasis, vol. 19, pp. 309–321, 1989.

U. Larsson, "Fibrinogen and its Conversion to Fibrin Studied by Biophysical and Biochemical Methods," Depts. of Coagulation Research and Medical Biophysics, Karolinska Institute, Stockholm, Dec. 17, 1987.

"Laboratory Equipment, Becton Dickenson Microbiology Systems—Diagnostics/in vitro Microbiology," http://www.bdms.com/search97.html.

"Electra Systems Brochure," Hemoliance, 1996.

"Electra Series Brochure," Medical Laboratory Automation, Inc., Jul. 1991.

"The MI A Electra 700 Automatic Coagulation Timer," Medical Laboratory Automation, Inc., Jun. 1991.

* cited by examiner

BLOOD COAGULATION ANALYZER

BACKGROUND

1. Field of the Invention

This invention relates generally to the field of blood coagulation analysis and more specifically to a method and apparatus for quantifying blood coagulation factors.

2. Related Art

In the field of clinical laboratory medicine, in the area of hemostasis, it is often desired to monitor the coagulation process of blood in order to determine how various factors in a blood sample impact the clotting time of the sample. Blood coagulation is a complicated process involving a large number of blood components including fibrinogen and prothrombin. Prothrombin is a protein that is activated by an enzyme complex formed on the site of an injury to produce thrombin. Thrombin cleaves fibrinogen molecules prior to fibrin polymerization to produce fibrin molecules that aggregate and form a blood clot. By monitoring components such as fibrinogen and prothrombin levels within the blood, a physician may acquire meaningful data concerning a patient's blood clotting abilities or other clinical conditions.

The proteins that are involved in the blood clotting process are commonly referred to as factors. The factors are numbered I–XIII, and reference to a factor by its number identifies the corresponding protein to those of skill in the art. The activation of prothrombin occurs as a result of the action of blood clotting factor Xa, which is formed by the activation of Factor X during proteolysis. There are two molecular pathways that lead to the activation of factor X to give Xa, generally referred to as the extrinsic and intrinsic pathways for blood clotting. The extrinsic pathway utilizes only a tissue factor specific to the injured membrane while the intrinsic pathway utilizes only factors internal to the circulating blood. Both of these pathways originate with the interaction of enzymes involved in the blood clotting process with surface proteins and phospholipids.

Various tests have been introduced to measure the coagulation process in both the extrinsic and intrinsic pathways of a patients blood sample. For example, the Activated Partial Thromboplastin Time (APTT) Test measures the coagulation factors of the intrinsic pathway. These factors include Factors XII, XI, X, IX, VIII, V, II and I which may be abnormal due to heredity, illness, or the effects of heparin therapy. Thus, the APTT test is useful as a presurgical screen and for monitoring heparin therapy. Similarly, the testing of the fibrinogen polymerization rate using a Thrombin Time (TT) test or a quantitative fibrinogen test provides useful diagnostic data.

Substantial efforts have been made to measure the level of the clotting factors during coagulation, particularly that of fibrinogen because it is one of the key factors in the clotting process. Most methodologies rely upon either immunologic or clotting techniques. Although immunologic techniques are generally capable of precisely defining the levels of the various components within the blood stream, they are often incapable of distinguishing between functional and non-functional forms of the components within the blood stream. Accordingly, immunologic techniques are felt to be less accurate at measuring blood clotting factors than clotting techniques.

Clotting techniques use coagulation timers to measure the elapsed time between the addition of a coagulation stimulating reagent to a blood sample and the onset of coagulation or fibrin polymerization. Coagulation instruments have been used for performing a variety of clinical chemistry tests such as a Prothrombin Time (PT) or Quick Test; an Activated Partial Thromboplastin Time (APTT); and a fibrinogen assay such as a Clauss Test.

Typically most clot detection instruments detect the formation of a clot in a patient's blood sample by monitoring either optical turbidity or mechanical properties of the patient's blood sample. The Fiberometer (manufactured by Beckton-Dickinson Microbiology Systems of Sparks, Maryland) is an example of an instrument which determines coagulation time by mechanical means. In such an instrument a timer runs only if an electrical switch contact which is immersed in the sample can be opened and closed repetitively. When the fibrin clot immobilizes the switch contact the timer is forced to stop. Other similar mechanical methods utilize magnetic fields to move metal balls or rods immersed in the clotting test sample by which means a timer is stopped when the fibrin clot immobilizes the device. Coagulation instruments based an optical methods tend to measure the "onset" of clotting, rather than the formation of a clot as determined by the above described mechanical methods. Optical turbidity may be determined by measuring the decrease in light transmission through a blood sample due to the formation of a clot. Basically optical coagulation instruments tend to detect relatively short strands of fibrin prior to the clot point.

According to one prior art method of determining the chemical factors present in the patients blood sample, the clot time of the patients blood sample, measured using either the optical turbidity or mechanical technique, is compared against a calibration curve. The calibration curve predicts the probable concentrations of factors for the patients blood sample according to the measured clot time. The calibration curve is generated in response to a series of clot time tests, performed on various dilutions of a control plasma sample. Thus, when an unknown patient sample is tested, the sample's clot time is converted to a factor concentration using the calibration curve.

One problem inherent in the prior art techniques for determining factor concentration is that the determinations are made at a qualitative, rather than a quantitative level. As such, the accuracy of the results is often suboptimal. Indeed, it is difficult to determine multiple factor concentrations from a single clot time measurement, at least in part because it is difficult to consistently identify the intended spot signifying clot time on the measurement waveform.

Traditional clinical chemistry equipment that measures such things as glucose do so by very quantitative means which readily relate to simple chemical reactions. In contrast, blood coagulation is a highly complex chain of chemical reactions. Coagulation timers seek to measure a parameter which correlates poorly to the chemistry which causes coagulation. They have therefore conventionally employed a qualitative measure. The instruments measure a gelling of a sample. That the gel forms is deterministic. The strength of the gel formed is also deterministic. However, the relationship between changes in physical properties over time as the gel forms and the initial chemistry is not highly correlated. Yet, conventional methods measure such physical properties. Optical methods repeatedly bombard the gel with beams of light and obtain results that indicate the operation of the chemistry. However, although these methods indirectly measure the chemistry of interest, they do not directly measure the chemistry. That indirection is one weakness of the prior art because formation of the clot never occurs exactly the same way, even in identical samples.

Thus, a problem exists as to how to create a good analytic model that translates a poorly correlated measured parameter event into a meaningful chemistry or chemical assay. While the above described hardware implementations generally provide acceptable results, such qualitative analysis lacks accuracy, as explained above, and yields only a narrow range of useful information.

SUMMARY OF THE INVENTION

According to one aspect of the invention, a non-linear logistic equation is provided that precisely matches the optical density, transmission or turbidity versus time of a clotting sample. The equation may be curve fit to a signal representing the optical density and/or turbidity of a blood sample. The equation provides as an output a set of coefficients which can be used directly, or converted by calibration curves or trained neural networks, to identify physical characteristics, such as clot time and fibrinogen concentration, of the blood sample. By using such an equation, quantitative tools for identifying the underlying chemistry of the blood clotting process may be provided. The coefficients of the logistic may be advantageously translated to identify physical characteristics of the blood sample through the use of multi-variate calibration curves or trained neural networks. Optimization logic may also advantageously be executed before the multi-variate calibration or use of a neural network to improve the performance of the inference engine by filtering exception conditions.

According to another aspect of the invention, a low level oscillatory signal is extracted from a clotting signal of a waveform. The clotting signal may be, for example, a signal of optical density, transmission, or turbidity versus time. The low level oscillatory signal may be used in a variety of manners. First, it may be used to compute a clot time by such means as, but not limited to, Fourier, FFT, wavelet, peak and minimum search, or by hardware means such as phased lock loops. Second, the low level oscillatory signal may be used to determine characteristics of the sample including kinetic reaction rates, reactant concentrations, abnormalities, or fibrin strand mass length ratio. The determination of the characteristics may be used to correct fibrinogen estimation through analysis of oscillation frequencies or time series profiles of the oscillation frequencies of a sample. Third, the extracted low level oscillatory signal may be used to compute initial starting coefficients for the logistic equation to thereby enhance the precision of the curve fitting operation.

According to another aspect of the invention, knowledge as to the underlying behavior of the clotting chemistry may be used to determine where to steer the bounds of the curve fitter to obtain initial estimates of the coefficients for the logistic. During the curve fitting process, for both the logistic and the polynomial equations, underlying knowledge regarding the chaotic characteristics of the clot waveform may be used to better weight individual data points to be curve fit, or adjust such things as sum of squares error. By using such a technique, the chaotic parts of the signal may be either filtered out or highlighted, depending upon the needs of the consumer.

According to another aspect of the invention, an apparatus for verifying the functionality of a clotting analyzer includes clot simulation means, coupled to the clotting analyzer for providing a simulated clotting signal, wherein the simulated clotting signal is provided using the non-linear function describing the entire clotting waveform. With such an arrangement, a straightforward method of providing a simulated clot waveform for testing clotting analyzer apparatus is provided that does not require storage of recorded clot waveforms.

The foregoing and other objects, features and advantages of the invention will be apparent from the following more particular description of a preferred embodiment of the invention as illustrated in the accompanying drawings.

DETAILED DESCRIPTION

Figure 1:
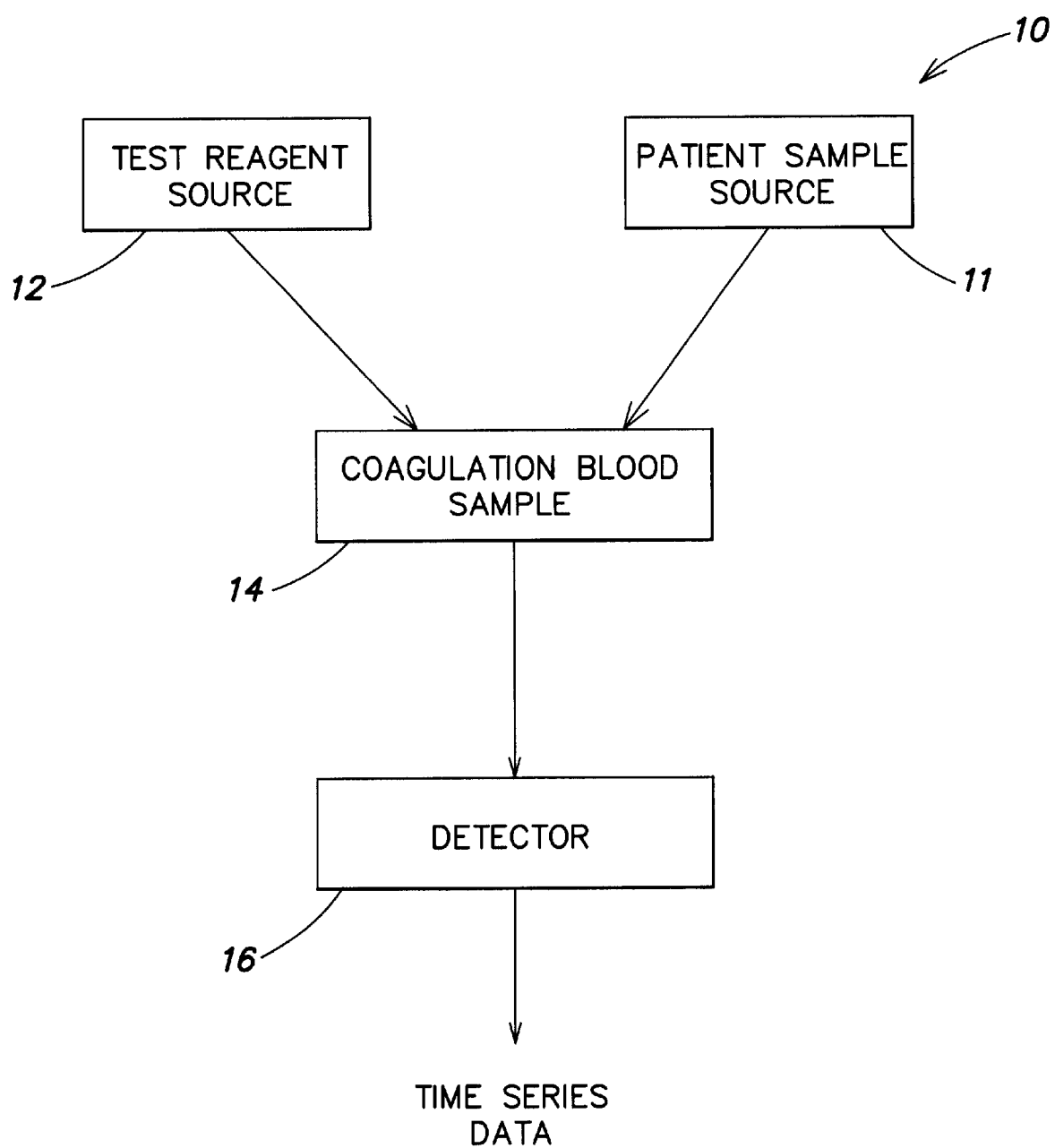
FIG. 1 is a block diagram of a system for obtaining a measurement of a blood clot event.

The present invention has applicability to several areas of analysis and synthesis related to blood clotting. Analysis refers to the reduction of collected time series data relating to a measured characteristic of one or more blood samples to a form more useful to the clinician or laboratory researcher. Synthesis refers to activities which produce predictions or simulated time series data corresponding to a measurable characteristic of clotting blood samples, measured overtime.

An analysis instrument embodying the invention can analyze time series data collected from one or more blood samples while they clot to produce such information as convention clot times customarily used by clinicians and described in the Background section, and blood factor assays which may be of greater use to future clinicians. Analysis can also produce information of use to those laboratory researchers studying blood clotting dynamics.

A synthesis, modeling or simulation instrument embodying the invention can synthesize time series data representing a measurable characteristic of blood clot events which would be expected to take place in hypothetical blood samples comprised of varying factor levels, including standardized calibration factor levels. Synthesis can predict the result of varying in a blood sample levels of various clotting factors, and can create time series data whose waveforms, when plotted represent clotting events resulting from standardized assays which are useful for calibrating analysis instruments, for example.

This inventor has discovered that a measurement over time of certain characteristics of a clotting blood sample includes information which correlates well with the concentration of each of the clotting factors desired to be assayed. The characteristic measured may be optical turbidity of the sample, i.e., optical density as an indication of turbidity, as used in the exemplary embodiments described, or may be one of several other measurable characteristics known to the skilled artisan. This inventor uses optical turbidity because it represents well the many complex chemical interactions occurring during the progress of a blood clot. There are a variety of useful methods for measuring the chemical status of the coagulation process. For example, Medical Laboratory Automation (Pleasantville, N.Y.) has traditionally designed and manufactured instruments (e.g., ELECTRA 1600C) that are based on photometric methods that make use of time changing light transmissivity during fibrin polymerization. Turbidity may be optically sensed by the decrease in light transmission through a blood plasma sample due to the formation of a clot. It does not matter whether the optical readings are taken directly off the main optical axis or off axis as in more detailed differential turbidity measurements. A voltage or current representative of the turbidity of the sample is provided by a detector. Alternatively, the measurement of fibrin polymerization over time may be performed by acoustic, rotating or vibrating magnets, or oscillatory electric fields means. Thus, although the below disclosure describes using optical turbidity measurements, the present invention is not limited to such a technique, and other available fibrin polymerization measurement techniques may alternatively be used.

Aspects of the present invention may be practiced using a variety of mathematical models of a blood clot event. For example, polynomial and sigmoidal models have long been used, and are still useful in connection with the invention. This inventor has developed a new, preferred model of blood clot events.

This inventor's new model of a blood clot event characterizes time series optical density data using both analytical mathematical techniques and chaotic mathematical techniques. Moreover, the parameters of both the chaotic and analytic portions of the model relate back to the physical reaction process.

Information obtained at different points in time during a clot event correspond to different portions of the clotting reaction, and therefore have been found to represent the effect of different clotting factors on the clotting process. By correlating backward from the parameters of the chaotic and analytic portions of the model, the underlying factor assays can be derived. Because each factor relates to multiple parameters, multi-variate backward correlation transforms the parameters of the model into factor assays.

The following, more detailed discussion, presents the model employed by this inventor, fitting the model to time series optical density data, deriving factor assays from the fitted model and deriving time series optical density simulation data from factor assays. The model which includes an analytical component and a chaotic component is first described. The description reveals how different information may be obtained from different time segments during the course of the clotting measurement. The different information corresponds to different portions of the clotting reaction and therefore represents the effect of different clotting factors on the reaction process.

Several different exemplary embodiments exploit different features of the model to fit the model to the time series data.

Next, derivation of factor assays by multi-variate back correlation, for example using neural networks is described. The result of back correlation may be a factor assay, a predicted time correlating to one of the conventional tests, etc.

Finally, correlation of model parameters to factor assays are described. Such forward correlation is then shown to be useful for simulating optical density data which would result from various factor assays.

For purposes of this initial, general discussion, clotting is assumed to take place in and be measured by a coagulation analyzer 10 of the illustrative embodiment shown in FIG. 1, which includes a test reagent source and delivery system 12 and a patient sample source 11. The test reagent source and delivery system 12 may include, for example, a thermo-electrically cooled disposable reagent cup and peristaltic pumps. The reagents may be, for example, a PT reagent, an APTT reagent, or a Clauss reagent, or another similar chemical that is used to encourage coagulation of the sample source. The reagent and the patient sample source are combined together to form a coagulation test sample 14 that is forwarded to a detector 16. The detector 16 is advantageously capable of providing measurement data on the chemical status of the test sample's coagulation reaction, for example time series data representing optical density.

The Model

This inventor has developed a model whose initial conditions are determined by chaotic behavior of the underlying clot chemistry. The model is roughly separable into three parts by frequency. There is a high-frequency oscillation whose characteristics are determined by early, chaotic events in a clot. This high-frequency component begins at or near the introduction of an initiating reagent and continues well past the more active portions of the clotting process, as described below. There is a mid-frequency component which is well-modeled by the second derivative of a logistic function. Finally, there is a low-frequency component which is well-modelled by a logistic function. The chaotic process which takes place following introduction of the clot-initiating reagent and before the clot cascade substantially gets underway determines how soon after introduction of a clot inducing reagent, the clot waveform commences. As seen below, insight into this chaotic process may be had by observing the high-frequency oscillation.

The analytical, i.e., non-oscillatory, portion of the model is now described mathematically.

For some coefficient values a plot of the equation model function (Equation (1), below) developed by this inventor can be made to substantially match a plot of a typical clotting waveform, e.g., an optical turbidity measurement over time. The equation model (Equation (1), below), which is a function defined by the sum of three terms, is dominated by a logistic dose function defined by the values of one or more coefficients. A clotting waveform corresponding to the sample source 11 is defined by time series data 17.

The waveform produced by this model can be approximated by relatively simple, calculus-based computer models which assume an oscillatory flow of raw materials into fibrin polymerization. The approximation uses an integrator to simulate polymerization. The model has also been tested by using computerized compartment models of the process, with initial process compartments including positive feedback loops. The results of this verification modeling demonstrate that the complete model is an integrated whole, clearly related to the underlying physical process.

$$OD(t) = a + \frac{b+ht}{1+\left(\frac{t}{c}\right)^d} + \frac{2eg^2\left(\frac{t}{f}\right)^{(2g-2)}}{f^2\left(1+\left(\frac{t}{f}\right)^g\right)^3} - \frac{eg(g-1)\left(\frac{t}{f}\right)^{(g-2)}}{f^2\left(1+\left(\frac{t}{f}\right)^g\right)^2} \quad (1)$$

When plotted, the function of the equation model mimics the changes in optical patterns of light transmission, optical density, or turbidity over time of a sample undergoing clot formation. As seen below, a set of coefficients can be related to the chemistry of the coagulation process. The function of the equation model can be curve fit to the time series data, i.e., coefficients selected which cause the plot of the logistic dose function to closely track the time series data. The values of the coefficients or combinations of coefficients then correlate with factor concentrations.

The Offset

As noted above, the equation model of Equation (1), includes three terms: a baseline offset represented by coefficient "a", a logistic function that tracks the fibrin polymerization of a clot formation, and a second derivative of a logistic function that represents the transient in optical density occurring at the onset of polymerization. The baseline offset "a", is a parameter relating to the given instrument performing the clot analysis. The offset compensates for variations in performance of the optical components of the coagulation analyzer 10 of FIG. 1 or other measurement system used.

The Logistic Functions

The logistic function that tracks the fibrin polymerization is defined by coefficients "b", "c", "d", and "h", where coefficient "c" is the centroid location of the logistic function, where the centroid of the logistic function is the center of mass of the function. Coefficient "c" also represents a time value which makes the most ideal candidate for an excellent reported clot time, as will be described later herein. Coefficients "b" and "h" comprise values which correlate with estimates of fibrinogen concentration. The logistic function is defined by (2):

$$\frac{b+ht}{1+\left(\frac{t}{c}\right)^d} \quad (2)$$

The coefficients of the logistic function that represents the transient beginnings of the visible onset of polymerization need not be the same as for the logistic function that tracks the fibrin polymerization. Moreover, the logistic function that represents the transient beginnings of the onset of polymerization is not tightly correlated temporally to the logistic function that tracks the fibrin polymerization; hence, the coefficients of the second derivative of the logistic function that represents the transient in optical density occurring at the onset of polymerization differ from those of the logistic function that tracks fibrin polymerization. The coefficients of the second derivative of the logistic function that represents the transient in optical density occurring at the onset of polymerization are "e", "f" and "g", and the second derivative defined by Equation (3), below is:

$$\frac{d^2}{dt^2}\left[\frac{e}{1+\left(\frac{t}{f}\right)^g}\right] = \frac{2eg^2\left(\frac{t}{f}\right)^{(2g-2)}}{f^2\left(1+\left(\frac{t}{f}\right)^g\right)^3} - \frac{eg(g-1)\left(\frac{t}{f}\right)^{(g-2)}}{f^2\left(1+\left(\frac{t}{f}\right)^g\right)^2} \quad (3)$$

Coefficient "f" represents a point in time corresponding to the centroid of the second derivative function. Coefficient "f" correlates with the reported clot time produced by blood clot timers that are based on first as well as second derivative algorithms. Coefficient "f" thus provides a clot time which correlates closely to the historical clot times of optical based coagulation instruments and provides results which track those produced by historical designs with regard to PT activity testing. The coefficient "f" comes closest to the historical definition of clot time as the "onset of clot formation", i.e. the onset of fibrin polymerizations. Coefficient "f" tends to, but does not always, lead in time relative to the previous temporal coefficient "c."

Coefficients "a", "b", "c", "d", "e", "f", "g", and "h" of Equation (1) correlate to coagulation chemistry variables, i.e. the initial factor concentrations. These coefficients can be extracted from a curve fit of the model equation to the observed time series data. These coefficients can be used to estimate clot time as well as the initial chemical concentrations of the sample source.

Figure 2A:
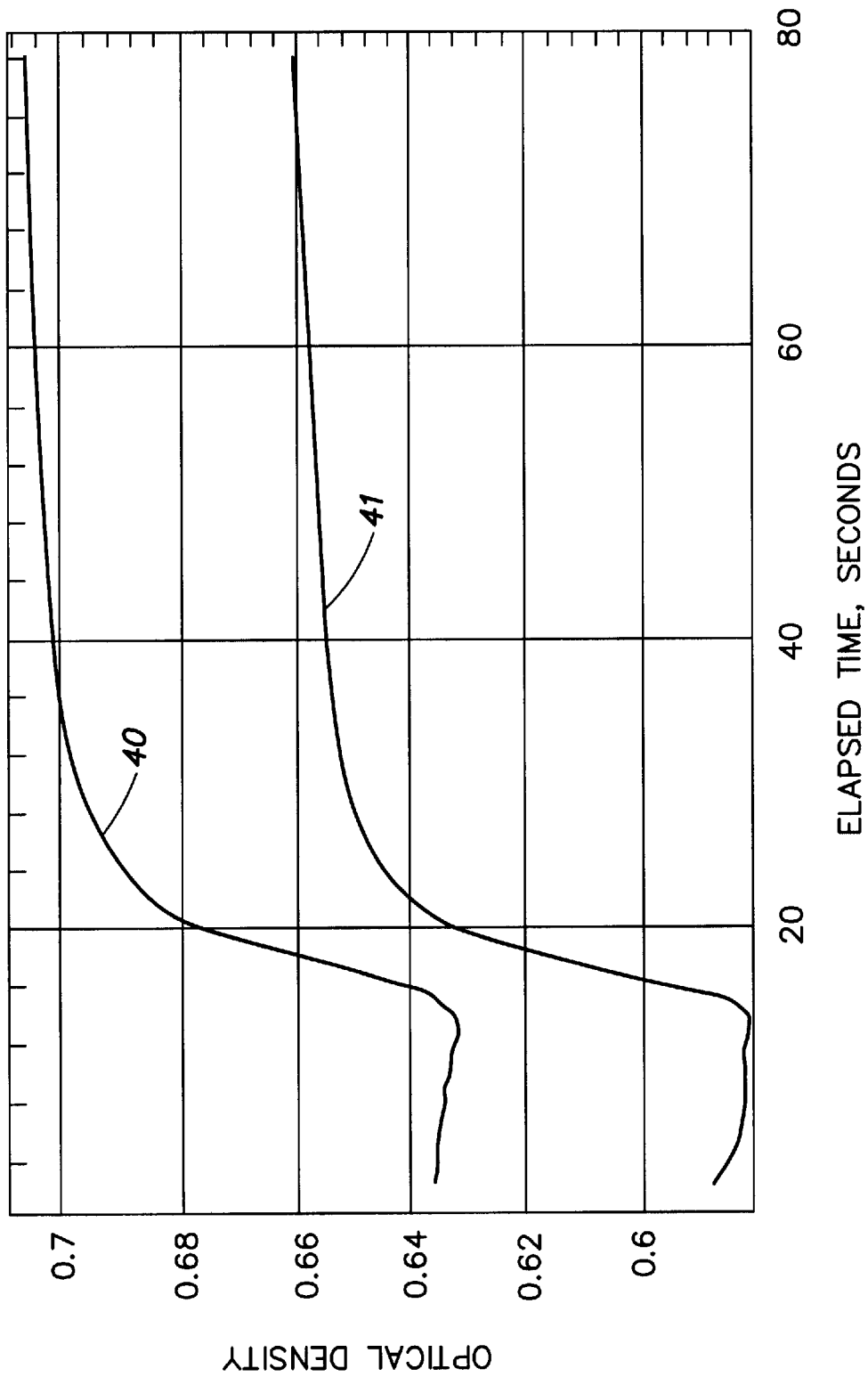
FIGS. 2A and 2B are timing diagrams illustrating an actual clotting waveform and a curve fit waveform provided using the non-linear function of one embodiment of the present invention.
Figure 2B:
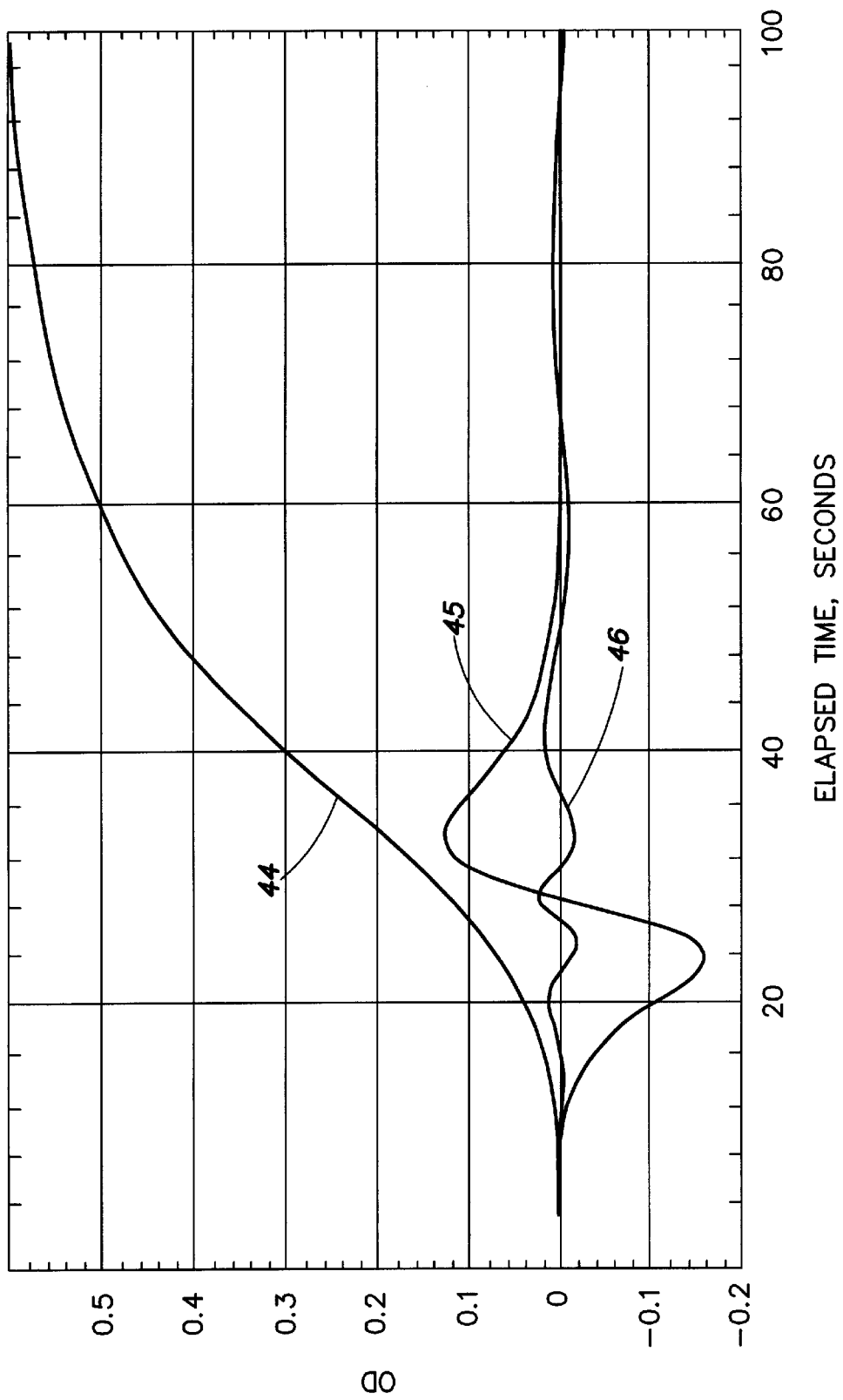

Referring briefly to FIGS. 2A and 2B, a series of clot waveforms illustrates the use of the equation model for simulating a clot waveform. FIG. 2A illustrates a clot waveform of a patient sample 40, measured in terms of Optical Density (cm) vs. Elapsed time (seconds). In addition, FIG. 2A illustrates a plot of the curve fitted waveform 41 obtained using the equation model set forth in Equation (1), and a Marquardt-Levenburg curve fitting technique. Curves 40 and 41 have been separated in baseline amplitude for ease of visualization. FIG. 2B illustrates the discrete time-varying components of the fitted clot waveform of FIG. 2A. The main logistic component 44 is the component provided by Equation (2). The second derivative of the main logistic component 45 is the component provided by Equation (3). In addition, a third component, indicated as oscillatory component 46 is shown.

The Oscillatory Component

As shown in FIG. 2B, the oscillatory component 46 is a residual curve obtained by subtracting the values of the function of Equation (1) as curve fit to the optical density signal from the optical density signal at each point in time. Because it is a residual of the curve fit operation, traditionally it has been treated as an undesired artifact and consequently filtered out as background noise. However, this inventor believes that the oscillatory component of the time series data waveform provides important information about the fibrin folding characteristics of the sample. This inventor expects this hypothesis to be borne out in controlled, scientific studies. Hence, it is treated here as part of the model, rather than an unwanted artifact.

The oscillatory component 46 has a shape somewhere between a sinusoid (sin θ) and a sine-squared ($\sin^2$ θ), and varies in frequency over the period of the clot. It is at its highest frequency at the moment that large scale polymerization begins. The peak frequency of oscillation is highest for short clot times and lowest for long clot times. The reported instrument clot time tends to be proportional to the reciprocal of the frequency of oscillation, at least in the cases of PT and Clauss measurements. The frequency of the oscillatory signal is also proportional to the derivative of the overall clotting signal.

The oscillatory component 46 can be extracted from the time series data produced by the measurement system by performing a series of short polynomial-based detrending operations across the time series data to effectively minimize the logistic components. Detrending also can reduce or remove the effects of external noise on the time series data waveform.

Noise reduction using detrending can be selectively performed on a portion of the time series data waveform. The noise reduced portion is then joined with untreated portions of the time series data waveform by interpolating between the points to be joined.

Note that the three time varying terms of the model, a logistic, a second derivative of a logistic and an oscillation, exhibit frequencies in three different ranges. These correspond to different stages in the clotting process.

The oscillatory term is thought to correspond to events early in the clot process, which are chaotic in nature. The oscillation appears to start at about the point where both thrombin and fibrin come into play. In PT and APTT tests, there is a delay until thrombin and fibrin are involved, thus delaying appearance of the oscillation. In a Clauss test, where thrombin is added as the initiating reagent, oscillation starts immediately.

In order for fibrinogen molecules to link together, the fibrinogen undergoes a folding, locking and unfolding process. Fibrinogen has three strands having two primary bond sites for calcium, referred to as the $\alpha$ site and the $\beta$ site. The $\alpha$ site is usually dominant. However, for a time the fibrin oscillates between the $\alpha$ and $\beta$ bond sites, producing the observed oscillation in optical density, seemingly stalling the clot process. Eventually, large scale bonding breaks the stall.

The oscillatory term thus provides information based on the underlying chemical processes that may be used in clot prediction algorithms. For example, the oscillatory term may be used to determine kinetic reaction rates, reactant concentrations, abnormalities, or fibrin strand mass/length ratio. Knowledge of the above characteristics allows for correction of such things as the fibrinogen estimate for a sample.

For example, preliminary observations indicate that a higher than expected peak frequency of oscillation may be correlated to a greater than expected mass/length ratio, while a lower than expected peak frequency of oscillation may be correlated to a lower than expected mass/length ratio. The frequency of the oscillatory component is expected to be approximately 20% of the value of coefficient f. Coefficient f, in turn, is correlated well with PT-based fibrinogen measurement. Knowledge of the oscillation frequency may, therefore, aid in the calibration of the PFIB measurements, enhancing the accuracy of clot time predictions. Methods that may be used to analyze the frequency and characteristics of the oscillatory component include, but are not limited to, Fourier, FFT, moving FFT window, wavelet, peak and minimum search methods. By using the results of the analysis of the oscillatory component in conjunction with neural networks, fuzzy logic, and/or multi-variate correlations, the clotting results may be adjusted to account for unusual frequency profiles produced by the clotting sample.

The oscillatory component may additionally be used to determine the first point in time at which thrombin comes into existence in the patient's blood sample. In the oscillatory component 46 of FIG. 2B, at approximately 16–28 seconds, the first transition in the observed oscillation is the first indication of free fibrin in solution from the initial thrombin-fibrinogen reaction. This measurement is used to perform assays as in chromogenic based PTs and chromogenic based APTTs. In any classical clotting based factor assay, the key question is the moment in time that thrombin (factor IIa) comes into existence. The variations possible in polymerization of fibrin due to biologically produced differences in the particular fibrin, interferences from FDP, d-dimer and others serve only to confuse the measurement. Thus, the oscillatory component may be used to identify a point of significant interest in the clotting cascade, such as the point at which free fibrin appears.

Figure 2C:
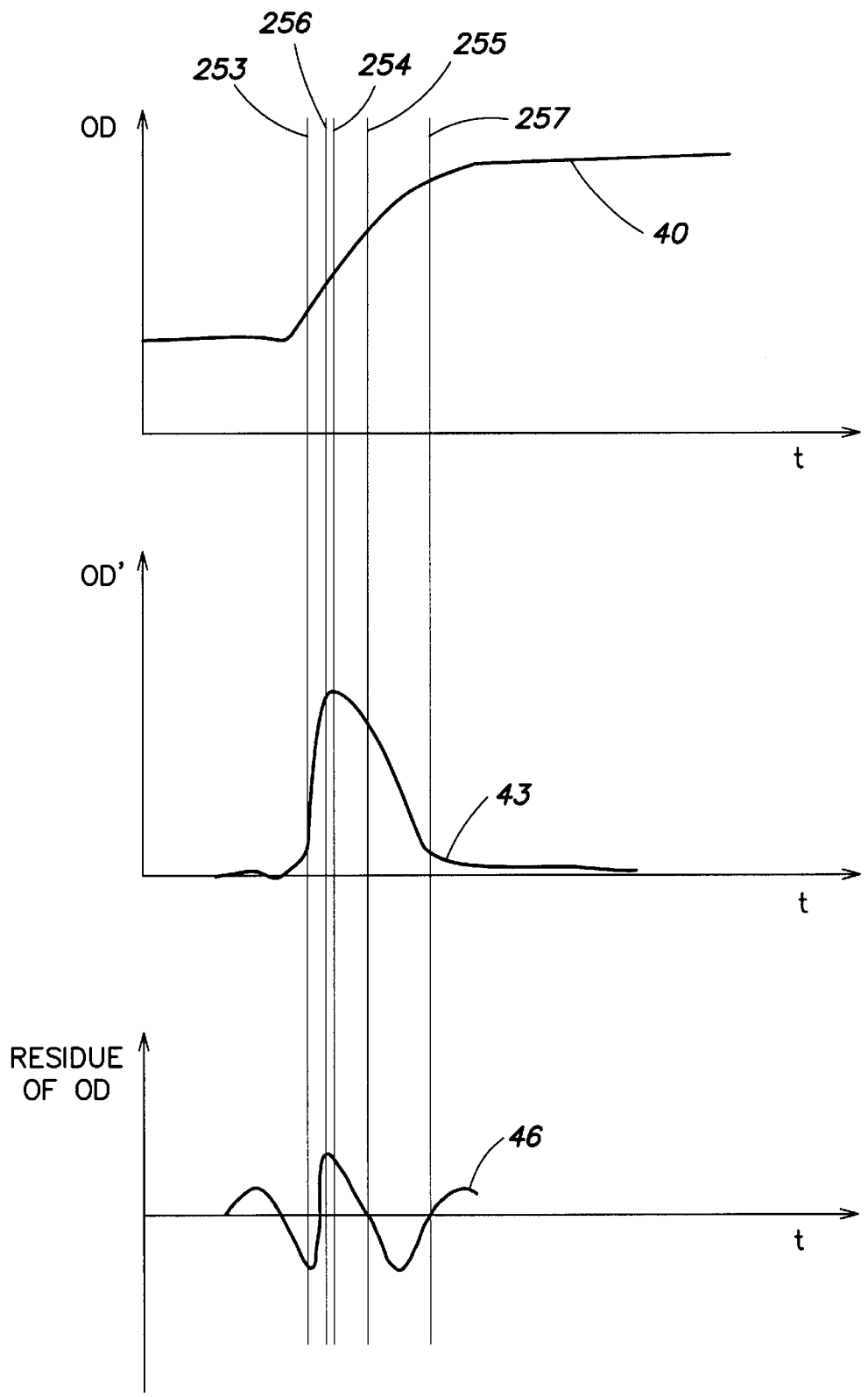
FIG. 2C is an exploded diagram illustrating the relationship between an oscillatory residual signal of FIG. 2B with relation to derivatives of the clotting waveform.

In addition, the oscillatory component may be used to provide a high accuracy clot time estimate for a given sample. Both the coefficient "c" and "f" of Equation (1) provide reasonable approximations as to the clot time of the sample. Referring now to FIG. 2C, a graph of a measured optical density waveform 40, the first derivative 43 of the optical density waveform 40, and the residual component 46 of the optical density waveform is shown.

Using the residual component 46, reasonable approximations of the coefficients of "c" and "f", hence reasonable clot time approximations, may be obtained. Optical density 40 and its derivative 43 begin to rise at time 253. The first minimum of the residual 46 occurs just after time 253, at which the optical density 40 and its derivative 43 begin to rise. Time 253 is the point in time conventionally reported as a clot time. The first peak of the residual 46 occurs at a time 256 just before the time 254 at which the peak of the derivative 43 of optical density 40 occurs. Time 256 is roughly equal to coefficient f. Coefficient c is just a little later, at time 255; roughly coincident with the zero crossing of the residual 46 immediately following the first peak. These approximations are useful in fitting the analytic terms of the model to actual clot waveforms, as explained below.

Finally, observing the oscillation as it decays following the main clot activity permits reliable determination of when measurement of a sample is complete. This determination is based on the frequency and amplitude of the oscillation, as it decays.

Alternative Model

An alternative model to which the following description and examples apply equally well, describes the optical density in terms of sigmoid functions, as follows:

$$OD(t) = a + \frac{b + ht}{1 + \exp\left(-\frac{t-c}{d}\right)} + \frac{d^2}{dt^2}\left[\frac{e}{1 + \exp\left(-\frac{t-f}{g}\right)}\right] \quad (4)$$

The logistic and sigmoid functions given differ slightly in symmetry about the centroid. The logistic-based model appears to have a better grounding in the physical reaction chain described.

Other models may also work, provided they possess a sufficient basis in the physical chemistry and a sufficient complexity to relate the large number of clotting factors to the OD measurement.

Fitting the Model to Data

Fitting the above-described model to measured clot data is now described in connection with the illustrative system of FIG. 3.

Figure 3:
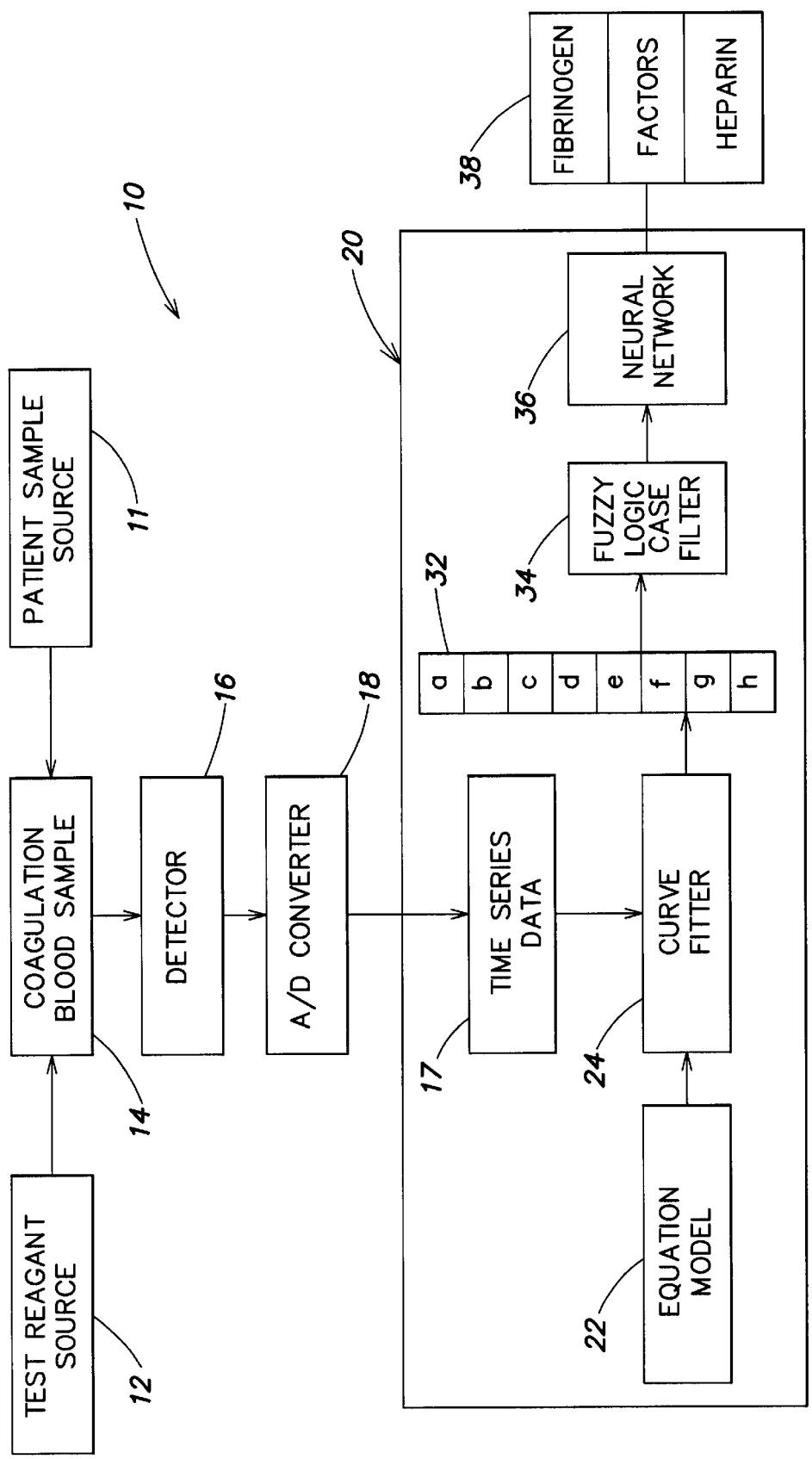
FIG. 3 is a block diagram of one embodiment of a clot analysis system according to the present invention.

The illustrative optical turbidity measurement system of FIG. 3 is characterized as follows, although the invention is not limited to this particular optical system. Coagulation analyzer 10 is substantially as described above in connection with FIG. 1. Optical turbidity measurements from the detector 16 are provided to an analog to digital (a/d) converter 18. The optical turbidity measurements are taken, for example, at a rate of ten per second and stored as time series data 17 in computer system 20. The a/d converter 18 converts the optical turbidity measurements, received in analog format from the detector 16, to digital format for use by a computational engine, such as a computer system 20.

The computer system 20 includes a memory for storing the received optical turbidity measurements as time series data 17. In addition, the memory stores a software program that analyzes the time series data 17 to determine the initial factor concentrations of the input sample 14; i.e., the concentrations of different proteins in the patients sample source 11. The software program in the computer system 20 includes an equation model 22 and an iterative curve fitter 24.

Curve fitting is a method of finding a simple curve $y=f(x)$ supplying the best possible approximation to the values $y_1, y_2, \ldots$ for discrete values $x_1, x_2, \ldots$ of the independent variable x. Any curve fitting technique known to those of skill in the art, such as the Marquardt-Levenburg curve fitting technique or variants of steepest descent curve fitting may be used in the present invention.

Preferably, the curve fitter 24 selects coefficient values for the equation model (Equation (1), above) such that the shape of a waveform produced by the equation model 22 'fits' the shape of the waveform defined by the time series data 17. Thus, the equation model 22 is used by the curve fitter to convert the raw, time series input data stream into a meaningful set of coefficient values 32. Alternatively, other functions, such as polynomials and sigmoid functions can be fit to the time series data 17.

One issue faced by practical curve filters is that they depend upon reasonable estimates for the coefficients, in order to produce good quality fits. The following Examples address this issue.

EXAMPLE 1

Finding a Clot Time Using the Oscillatory Component

One example of using curve fitting to analyze a time series of optical density data is to derive a high quality, i.e., highly repeatable, clot time.

Figure 4:
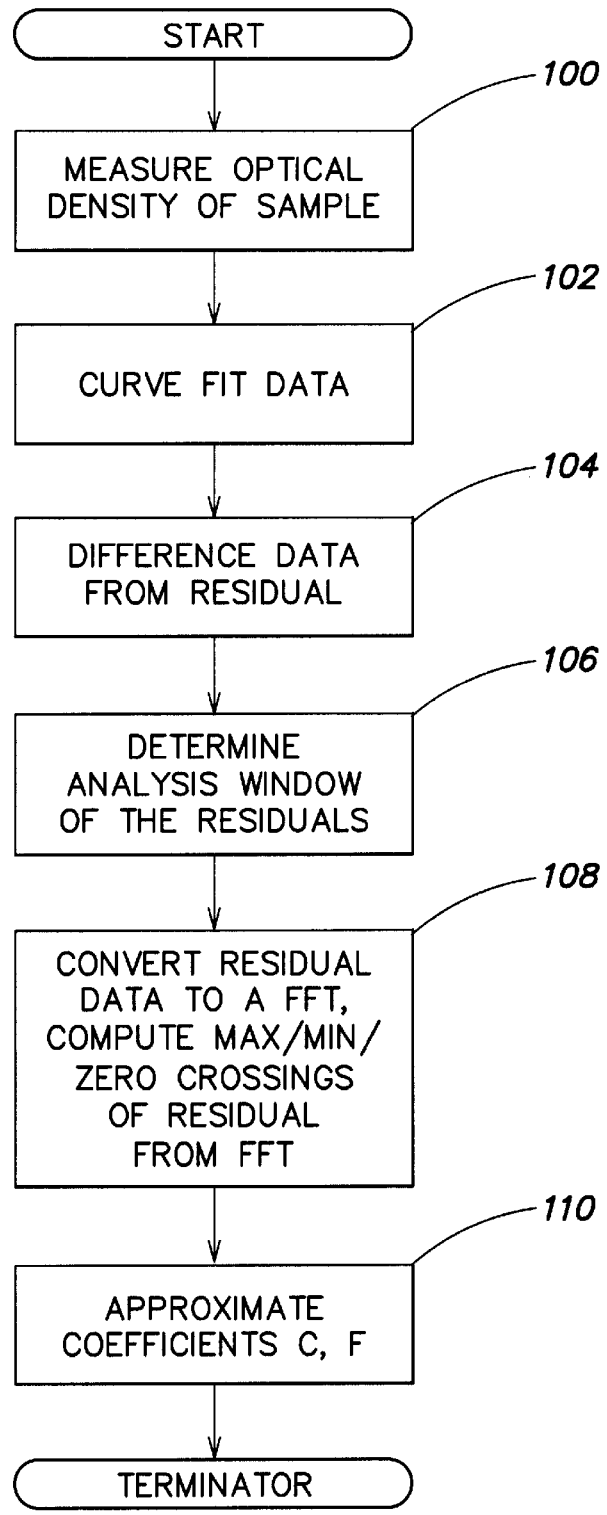
FIG. 4 is a flow diagram illustrating a process used to extract the residual from the clotting waveform and approximate coefficients of the non-linear function.

Referring now to FIG. 4, a flow diagram illustrating one method that may be used to derive a high quality clot time from a time series of optical density data of a patient's sample is shown. At step 100, the optical density (OD) waveform (FIG. 2C, 40) is obtained from the patient's blood sample. At step 102, a preliminary polynomial curve fit to the OD waveform is made.

At step 104, once the preliminary curve fit has been completed, the curve formed by curve fitting 102 is subtracted from the optical density waveform (FIG. 2C, 40), leaving the residual oscillatory component (FIG. 2C, 46). At step 106, a window of interest in the residual component is determined, where the window of interest identifies that portion of the residual component that includes relevant clotting information, as explained below. Iterative numerical minimization is used to find the peak location of the polynomial determined at step 102, indicative of the true maximum amplitude of the peak frequency in the residual component. This is done using a technique combining Fourier analysis and multidriven signal arithmetic. Fourier analysis permits the initial minimum of the oscillation to be found, based upon later, more prominent peaks. The closest adjacent points in time to the time of occurrence of the estimated frequency, i.e., the initial minimum, are located based upon Fourier analysis and the location of a prominent peak in the oscillation, and the Real (R), Imaginary (I), and frequency (F) components of the residual oscillatory component 46 are plotted in a multidimensional space. The below simultaneous Equations (5) are then solved using iterative numerical methods:

$$0 = f(F,R,I)$$
$$V^2 = R^2 + I^2; \text{ where} \tag{5}$$

$OD = R + iI$ and $i = \sqrt{-1}$; and where

V is the magnitude of the vector (R,I)

The window of interest is measured in terms of a time delay, which may be computed using the results described above and the formula $$\frac{1}{F} \arctan\left(\frac{I}{R}\right)$$

to determine a phase delay relative to the oscillation at an angle $\phi$ which corresponds to a time difference between a time when the source residual data was received and a time $t_0$.

At step 108, the residual component is analyzed to find the time at which the minimum peaks, maximum peaks, and zero crossings of the residual component occur. At step 110, the values for the coefficients "c" and "f" are determined using the below Equations (6):

$$f \approx t_{0,1}$$
$$c \approx t_{0,2} \tag{6}$$

where $t_{0,1}$ is the time at which the residual peaks (FIG. 2C, 256), immediately prior to the peak of the first derivative of optical density (FIG. 2C, 254), and where $t_{0,2}$ is the time at which the residual crosses the axis (FIG. 2C, 255) after the peak of the first derivative of the optical density waveform.

Thus, the oscillatory component may be used to provide initial estimates for coefficients "c" and "f". Moreover, as a bonus, both coefficient "c" and coefficient "f" may be used as clot time estimates. Coefficient "c", which is the centroid of the logistic function, provides a higher precision clot time estimate for duplicate pair differences of test samples. However, coefficient "f", the centroid location of the second derivative, provides a "clot time" which correlates more closely to the historical clot times of optical based coagulation instruments and provides results that track historical designs in regard to PT activity testing. Thus, coefficient "f" provides the closest approximation of the historical definition of clot time as the "onset of clot formation", and is therefore truly indicative of when polymerization begins.

A wide variety of alternative analysis methods known to those of skill in the art such as, but not limited to, Fast Fourier Transform, wavelet, peak and minimum search, or by hardware means such as phased lock loops may be used in connection with the above-described technique, and thus the invention is not limited to a particular analysis method.

As an example, a variation on this example is now presented. This variation is based in part on the relationship between the Fourier transform of the optical density, the sum of squares error and statistical properties of Gaussian distributions.

In the Fourier transform, the DC component corresponds to a mean, while each of the frequency components of an FFT correspond to an orthogonal squared Gaussian, similar to an individual sample in a standard deviation calculation. In statistics, there is a theorem that states a sum of a sufficiently large pool of non-Gaussian distributions approaches a Gaussian distribution. Consider, therefore, extending the analogy to an application of this theorem to the FFT frequency components.

Instead of finding a best fit, directly, as described above, this variation builds a table of probability distribution for the time differences between adjacently located time values in the solution set. This distribution bears a direct relationship to the residual oscillation—they mirror each other. Numbers of standard deviations from the mean, i.e., the DC component of the FFT, map to phase angles. Thus, coefficients "c" and "f" are computed based on phase angle as determined using standard deviations.

This variation tolerates adverse input data conditions better than the previously described method. Adverse input data conditions are those in which unusual initial conditions tend to lead to erroneous conclusions concerning clot time or factor concentrations.

EXAMPLE 2

Deriving Coefficients of the Logistic Functions Using the Oscillatory Component The coefficients of the logistic function may be obtained by curve fitting the logistic function to the time series data representing the clot event in the patient's sample. Accurately finding the coefficients may be a first step in assaying the patient's sample, as explained below. Curve fitting techniques make iterative guesses of possible coefficients, which are then inserted into the function, which is in turn tested for goodness of fit with the original time series data. In view of this process, and for a number of reasons known to those skilled in this art, a reasonable initial guess of the coefficients provides a faster and more accurate curve fit. Although initial estimates of coefficients "a", "b", "c", "d" and "h" may be made with adequate precision by performing Min(OD), Max(OD), $$\left(\frac{d}{dt}OD\right)$$

in connection with a calibration curve relating "a", "b", "c", "d" and "h" to such is of OD, the initial estimates for the coefficients "e", "f" and "g" are difficult to make.

As mentioned above, the oscillatory component 46 may be used to provide initial estimates of coefficients "f" and "c". In addition, the above methods may be extended to provide initial values for the coefficients "d" and "g" using the below Equations (7):

$$d \approx \frac{t_{256}}{(t_{253} - t_{257})} \quad (7)$$

$$g \approx \frac{t_{256}}{(t_{253} - t_{256})}$$

where the subscripts for the times forming the terms of Equations (7) refer to the times indicated by corresponding reference numerals in FIG. 2C.

EXAMPLE 3

Deriving Coefficients of the Logistic Functions Using the First Derivative

In an alternative method of deriving initial estimates for the coefficients, the first derivative of the optical density is used.

As shown above in Equation (1), the Optical Density (OD) is represented by a combination of the logistic given by Equation (2) with the second derivative of a logistic given by Equation (3). Thus, the first derivative of the clot's OD is a composite of the derivatives of the two functions. An example composite waveform of the first derivative of the OD is illustrated in FIG. 5A, in terms of OD' vs. Time.

The composite waveform 33 is a composite of the derivatives of the two functions which form Equation (3). Waveform 35 illustrates the portion of the composite waveform given by the derivative of Equation (3), while waveform 37 illustrates the portion of the composite waveform given by the derivative of Equation (2). As shown in FIG. 5A, there are two closely spaced derivative peaks, P1 (35a) and P2 (37a). The time at which peak P1 (35a) appears may be used to provide an initial approximation for the value of coefficient "f." The time at which the peak P2 (37a) appears may be used to provide an initial approximation of the value of coefficient "c".

Figure 5A:
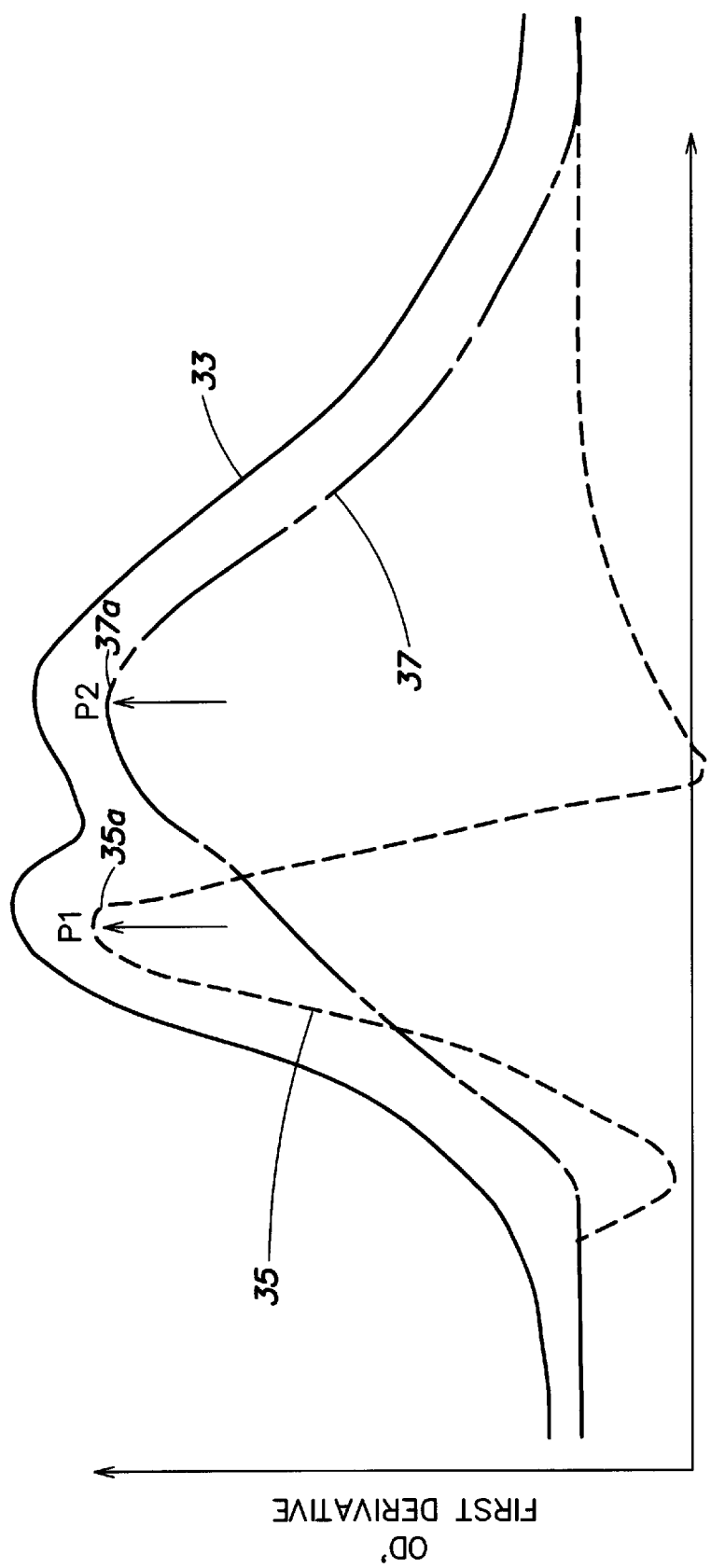
FIGS. 5A–5C are diagrams illustrating the composite nature of the first derivative of and second derivative of the clot waveform illustrated in FIG. 2B.
Figure 5B:
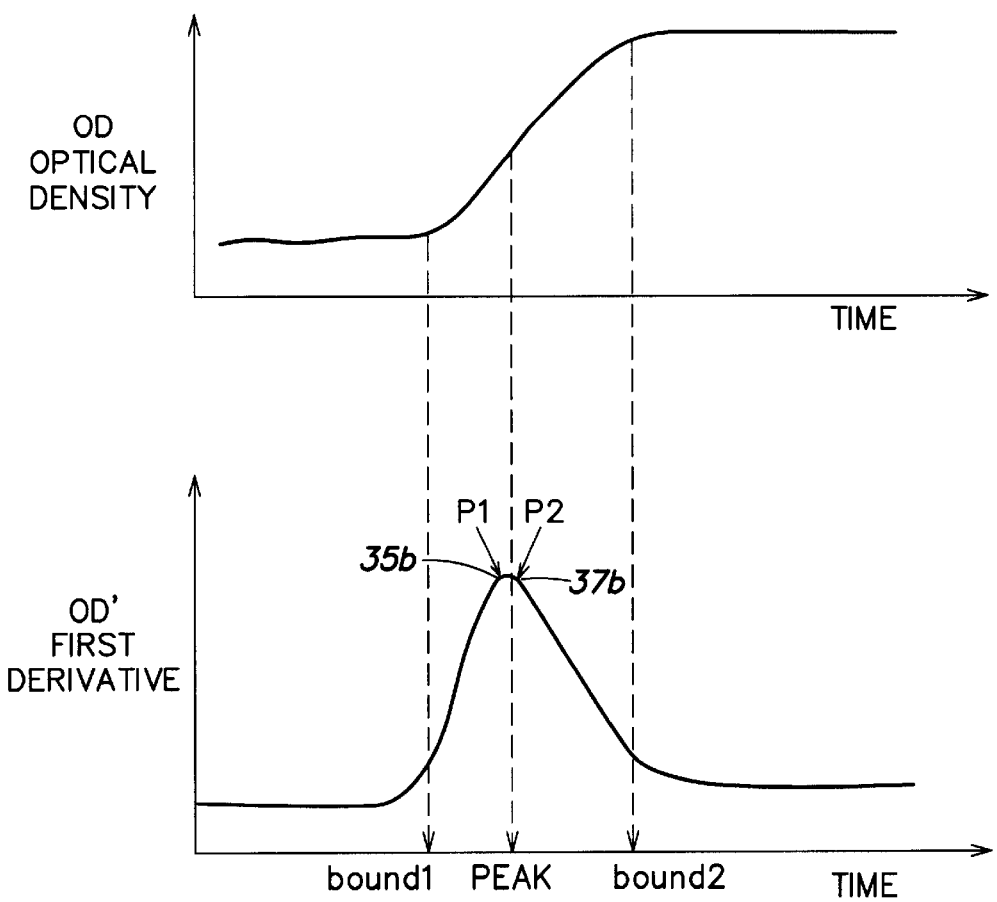

As shown in FIG. 5A, sometimes the peaks are spread far enough apart that the individual peaks P1 and P2 are distinguishable within the composite waveform 33. Often, however, the two peaks blend completely into one. One example of such a composite OD, waveform is illustrated in FIG. 5B, with the two peaks 35b and 37b marked in the composite. In such instances, in order to approximate individual times of peaks P1 and P2, elaborate signal analysis could be performed on the first derivative of the composite signal to discriminate between the two peaks. However, the signal analysis required to separate the peak is time consuming. Alternatively, simple peak searching techniques known to those in the art could be used to identify a peak of the composite. When the peaks are indistinguishable, such as in the composite waveform of FIG. 5B, typically the simple peak searching techniques are able to identify only one of the peaks of the first derivative: that peak that is closer to the coefficient "f". The value of the coefficient "c" is often difficult to discern, because it is masked by coefficient "f". However, because the first derivatives of Equation (2) and Equation (3) are closely spaced and tend to be numerically close in value, when estimating the initial values of the coefficients for the functions, some degree of uncertainty may be tolerated provided the approximations are close enough to stay out of predefined sub-optimal chi-square minima.

Accordingly, using the data provided by the first derivative of the composite signal, the values of the coefficients may be estimated by using the location of the first derivative peak as the estimator for both of the centroid locations "c" and "f".

Estimating initial coefficients of the function of Equation (1) that maps to the OD signal may be implemented using a topology search algorithm such as steepest descent. With steepest descent searching, the gradients of the chi square coefficient may be used as a tool to identify the shortest path to the bottom of the chi square surface, and thus to identify initial coefficient values.

When using curve fitting algorithms such as steepest descent, finding the best bottom location and not overshooting is difficult because the slope at the bottom of the chi square surface becomes very shallow and the best numerical precision practical for the computation combined with chaotic conditions of the data set become the dominant causes of variations within the slope.

One method of overcoming the imprecision of the calculations is to change strategies at the end of the search effort to interpolate a solution from the previously calculated search regions. Interpolation makes use of the known property of the bottom of all chi square surfaces that since the whole method is based on least square, normal distributions, the bottom shape can be closely approximated by a quadratic. By fitting a quadratic to the last searched values and testing to see if the zero crossing of the derivative of the quadratic is located somewhere in the middle of the last searched values, a final solution may be interpolated.

However, because the logistic portion of Equation (1) is non-linear, there are generally multiple chi square minima and multiple apparent solutions. Determining which solution is the best solution is difficult. In the case of the optical density waveform for fibrin polymerization, the shape of the waveform is quite complex with numerous bumps that may be events best described using the techniques of chaos theory. Accordingly, a preferable search strategy is to systematically cover the entire region of interest, cataloging all of the solutions and their associated sum of square errors.

Small sample sizes exacerbate the problem of obtaining accurate results from a lowest sum of squares error approach. Frequently, a small sample size leads to statistical errors such as over- or under-estimated standard deviation values or skewed distributions. These statistical errors in turn produce type II errors or $\beta$ errors when using Student's t and f tests, for example.

When using small sample sizes, particularly, other numerical solution approaches produce better estimates of coefficient "f" for example. Selecting as the solution the median or the mean of the set of candidate solutions produces better results than using the lowest sum of squares error solution, with the median producing the best solution overall.

Figure 5C:
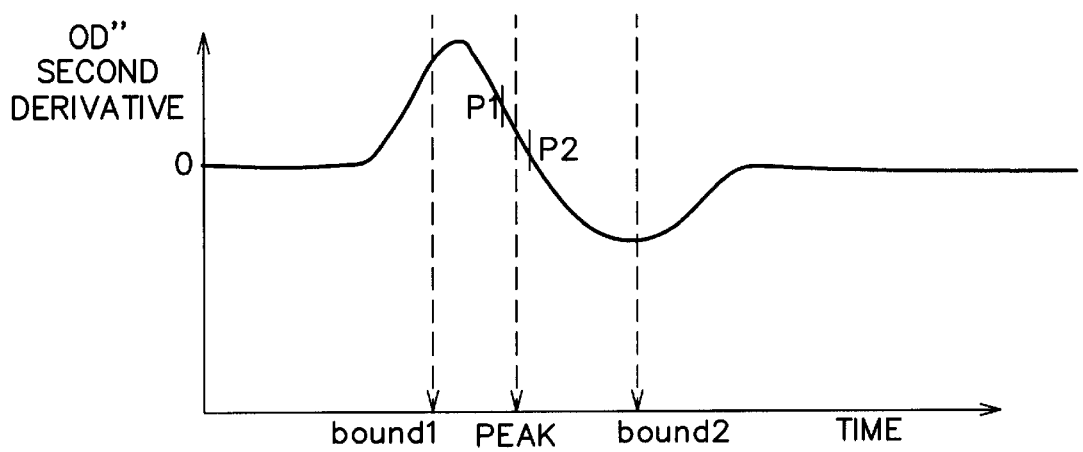

When initiating the curve fit of the logistic, the peak value of the first derivative of optical density versus time is identified. Next, using iterative search techniques, chi square error values are accumulated, stepping away from the peak in either direction to the limits of a bounded region; i.e., points in time denoted upper and lower bounds where the "useful" region of signals is separated from the useless region. The values for the upper and lower bounds may be obtained using the second derivative of the optical density waveform by simple search techniques to locate the maximum and minimum peak values of the second derivative of the OD, illustrated in FIG. 5C. However, one drawback of estimating the upper and lower bounds using the second derivative of the optical density signal is that the signal to noise ratio produced by a low fibrinogen concentration may be inadequate, producing less exact results than desired. Therefore, according to one embodiment of the invention, the first derivative of the optical density signal is used to approximate the upper and lower bounds by searching down the sides of the first derivative peak to locate a vanishing point, where the sides of the derivative peak essentially fade into the background noise of the signal.

It should be understood that the references to "noise" in the above sense is not meant to refer to the typical random, uncontrollable variation in the signal. Rather, it has been determined that the noise in the signal is chaotically related to the chemical process taking place, and therefore not simply random, but a mix of one or more variables which behave in a manner which is difficult to predict and therefore produce an unexpected result. The variables themselves may provide important insight to the clotting waveform, and therefore, according to one embodiment of the invention, are not simply ignored.

Figure 6:
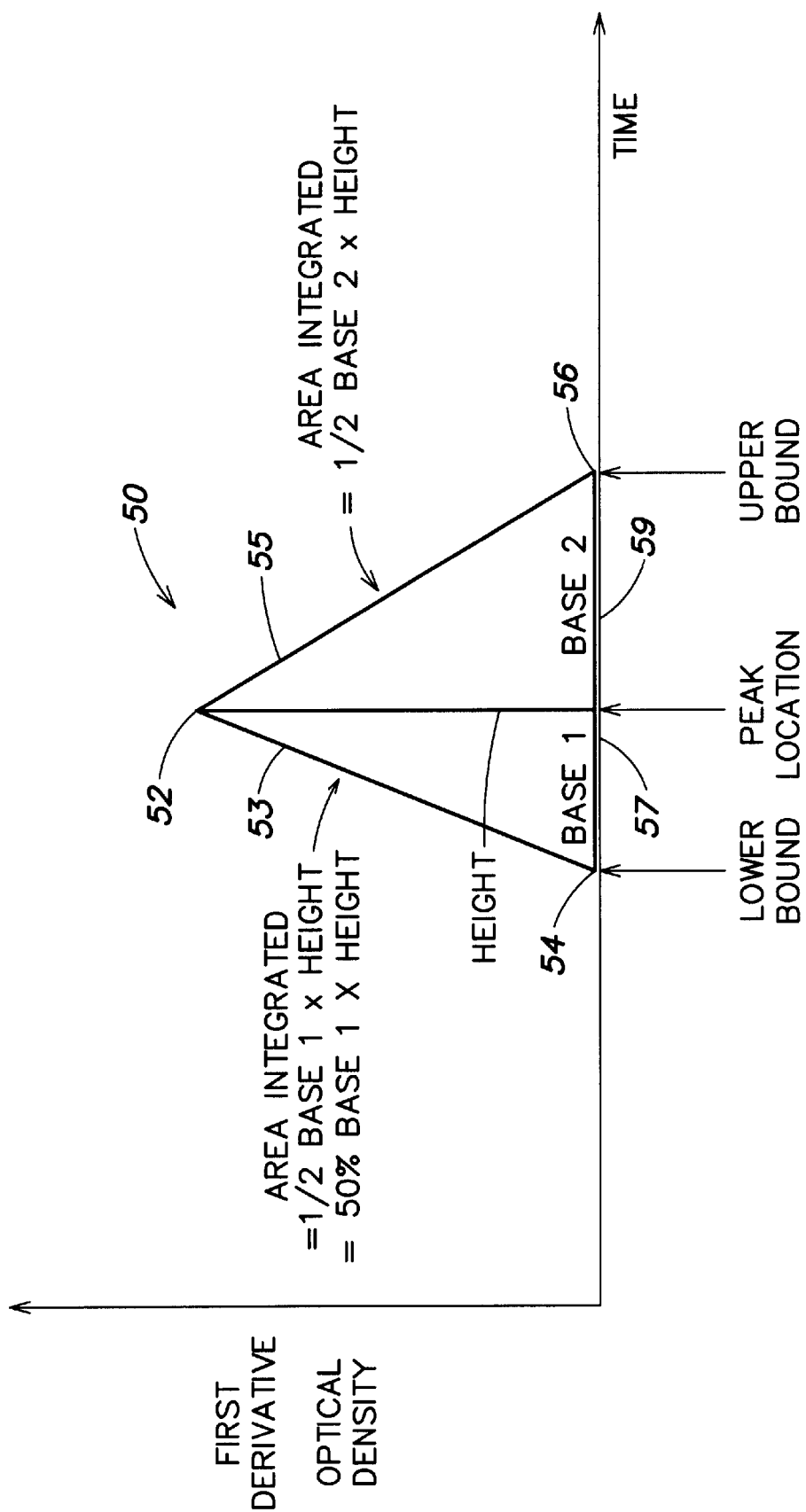
FIG. 6 is a diagram of a technique for conceptualizing the first derivative of FIGS. 5A and 5B for analyzing and estimating coefficients of the non-linear function.

Referring now to FIG. 6, the first derivative of the optical density signal may be conceptually represented in simplistic terms as two right triangles 53 and 55, adjoined along their height, forming a larger triangle 50. The height of both triangles is the first derivative peak amplitude 52. The triangle 53 has as it's base 57 the distance along the x axis from the first derivative peak 52 to the lower bound 54. The triangle 55 has as it's base 59 the distance along the x axis from the first derivative peak 52 to the upper bound 56.

Thus, the goal is to identify the useful region of analysis of the first derivative, which is represented by the values of the lower bound 54 and the upper bound 56. In one embodiment of the invention, when determining the values for the upper and lower bounds, the analysis of the first derivative of the polynomial is performed by traversing the first derivative from the peak 52 down the trailing edges in two phases. During the first phase, approximately half of the triangle is traversed from the peak down the trailing edges. Starting at the peak helps to minimize the effect of chaotic interference, which is often found in the leading edges of the first derivative of actual OD curves. The region between the first derivative peak of the data and the bottom of the trailing edge of the first derivative peak of data is a more chaos free region and accordingly the identification of the upper and lower bounds will be affected less by chaotic interference by beginning the traversal at the derivative peak.

The identification of the upper and lower bounds is performed using integration techniques (rather than differentiation techniques) to minimize the effect of noise in the results. During the first phase, the area of the triangle is accumulated by traversing downward along the edges 53 and 55 of the triangle 50 (and accordingly along the height of the triangle), and accumulating the area of the triangle until the height is approximately equal to 50% of the peak amplitude. The area of the right triangle is given by the equation $$\frac{base \times height}{2}.$$

Therefore, an iterative process may be implemented, using an average area per unit distance, and thus normalizing the base increment distances to a value of one such that the average amplitude is the only relevant number. The first phase of the process is completed when the amplitude used during the integration is approximately 50% of the maximum peak of the first derivative. One could alternatively use other cut-off percentages for terminating the first phase of the analysis, such as 40% or 60% and thus the invention is not limited to any specific percentage.

During the second phase of analysis, the traversal along the edges of the first order derivative may result in data points that are influenced by chaotic interference. As such, each time that one of the points of the edges 54 and 56 are selected, it is compared against a threshold that is a minimum percentage of the first derivative's peak value. Once the individual values fall below the threshold, and a match on the average value has been reached, the last points are selected as the upper and lower bounds of the first order derivative. Thus, noise is prevented from influencing the minimum values that define the upper and lower bounds of the first derivative of the optical density by maintaining an accumulated average of the data points, and selecting an average minimum threshold that allows the presence of noise to stop the search.

Once the upper and lower bounds have been determined, the initial values for the coefficients "d", "c", "g" and "f" may be defined by the system of proportionalities (8):

$$d \propto \frac{t_{p2}}{(t_{b1} - t_{b2})} \qquad (8)$$

$$c \propto t_{p2}$$

$$g \propto \frac{t_{p1}}{(t_{b1} - t_{p1})} \text{ and}$$

$$f \propto t_{p1}$$

EXAMPLE 4

Fitting a Sigmoid Function to the Optical Density

In this example, estimates are made for "f" and "c", subsequent to which a curve fit is performed.

Once the initial coefficients are selected, using either information gleaned from the oscillatory component (FIG. 2B, 46) or from the first derivative (FIG. 5A, 33), the curve fitter initiates the process of curve fitting a sigmoid function to the time series data waveform by iteratively manipulating the coefficients of the sigmoid function until a 'best' match is found between the two waveforms. Using the techniques of Example 3, above, during each iteration, the upper boundary identified above is used to search down the sides of the first derivative. The lower boundary has a variable time value added to it whose sum acts as the lower data boundary for the curve fitting operation. For each curve fit operation (which in principle moves the sigmoid slightly relative to the OD signal), the variable time value identifying the lower bound is stepped to a new value contained in a list of possible values.

The curve fitter includes a sum of squares error table. Each time that a curve fit operation is performed for a different lower bound value, the resulting coefficients and the chi square error result are stored in the table. The contents of the sum of squares error table are used to select the final coefficients for the sigmoid. However, before the values in the sum of squares error table are used to select coefficients, according to one aspect of the invention, each entry in the sum of squares error table is multiplied by a penalty. As will be described in more detail below, the penalty is selected to bias the values in the sum of squares error table to help identify the most likely candidates for the coefficients "f" and "c". After the respective penalties have been applied to each of the entries in the sum of squares error table, the sum of squares error are sorted to provide the table entry with the lowest sum of squares error.

Historically, the lowest sum of squares error was selected as the correct result. However, it is now realized that the various possible solutions generated in the search represent measures of the undulations in the OD waveform, and that the solutions can be related to the OD signal and to its oscillatory component as follows. The range of solutions produced using the above procedure spans the time between the peaks of the second derivative of the OD signal and also spans the space of one wavelength of the observed oscillation between the negative peak where the overall optical density begins to increase and the negative peak which occurs just past the peak of the first derivative of the optical density. The highest concentration or density of solutions occurs just after the positive peak of the observed oscillation, near the first derivative peak of the optical density. This region of the optical density versus time waveform does not have a clearly defined point which can be identified as a "clot time" because it has a substantially uniform slope and a length close to one wavelength of the observed oscillation. It is for this reason that prior methods, often using analog electronics and described as "first derivative" and "second derivative" methods had an excessive duplicate pair variance. That is, the variance in results of successive measurements of identical samples treated identically is excessive. The point in time that those earlier methods attempted to determine was indistinct.

Values within the sum of squares error table may be used to determine the final coefficients, with solutions related to the sum of squares error, the mean solution and the median solution relating to coefficient "f" of the logistic. The dominant span in numerical methods of the solutions relates to the spacing between peaks described by the part of the logistic equation using coefficients "e", "f" and "g". The highest valued, reasonable solution approximates coefficient "c".

Coefficient "c", which is the centroid of the logistic function, may be estimated by either the use of a penalty function or by sorting criteria such as the highest valued solution of time with acceptably high correlation coefficient and spaced no more than so many standard deviations from the mean solution of time, such as 3.1 standard deviations higher than the mean.

As mentioned above, according to one aspect of the invention, associated with each data point on the polynomial curve is a penalty value. The penalty value corresponds to the probability that an estimated centroid location at that data point is more or less likely to be the optimum estimated centroid location. The penalty values for each of the data points of the polynomial are stored in a penalty table.

The penalty value associated with each estimated centroid location in the sum of squares error table is applied to the sum of squares error for that location. The application of the penalty value to each of the estimated centroid locations helps to highlight the best selection for the estimated centroid.

As discussed previously, it is generally known that chaotic behavior occurs at the start of the fibrin polymerization process; i.e., on the lower bound of the first derivative peak. Consequently, the most relevant data points are those close to the upper bound of the first derivative peak. In addition, the estimated centroid location is expected to be below the first derivative peak location. Because the estimated centroid locations are more likely found below the first derivative peak location and because the estimated centroid locations at the lower bound of the first derivative are more than likely influenced by chaotic interference, the penalty values are applied to filter unlikely estimated centroid locations out of the potential data set stored in the sum of squares error table.

Thus, a penalty is applied to each of the estimated centroid locations in the sum of square errors table, with the value of the penalty selected according to the location of the estimated centroid within the sigmoid. The penalty function may be implemented as combinatorial logic, a look up table, or an equation which serves as a multiplier to modify the sum of squares error values in the solution set to favor selection of solutions better representing the coefficient "c", and decreasing the likelihood of selecting solutions more representative of the coefficient "f".

An example of an equation serving the purpose of a penalty function might be a quadratic polynomial function of the sum of squares error with coefficients that: 1) multiply the sum of squares error by a large number, such as 10, if the solution being considered is at the location of the peak of the first derivative of the optical density; 2) multiply the sum of squares error by a low number such as 1 if the region of the solution being considered is in the area one would expect the coefficient "c" to occur; and 3) multiply the sum of squares error by a large number such as 10 if the region of the solution being considered is near the upper curve fit bounds. The exact equation used and the specific multiplier values implemented can be arbitrarily chosen with a goal of enhancing the selection of the best solution. An alternative implementation would be to curve fit the sum of squares error versus time solution set with a function such as a quadratic to find the nominal trend, and then divide the sum of squares error by the function to produce a new array which represents the time solutions versus a ratio representing a variance ratio between the individual solution's variance and the overall trend. Then one would sort for the highest valued time solution with a sum of squares error lying close to the trend line, i.e., whose ratio is close to unity.

Although the above methods have been described using the first derivative of the optical density signal, the concepts of the above method may also be used to enhance the accuracy of other clot detection methods, including polynomial template algorithms of the prior art.

EXAMPLE 5

Fitting a Polynomial Function to the Optical Density

Figure 7:
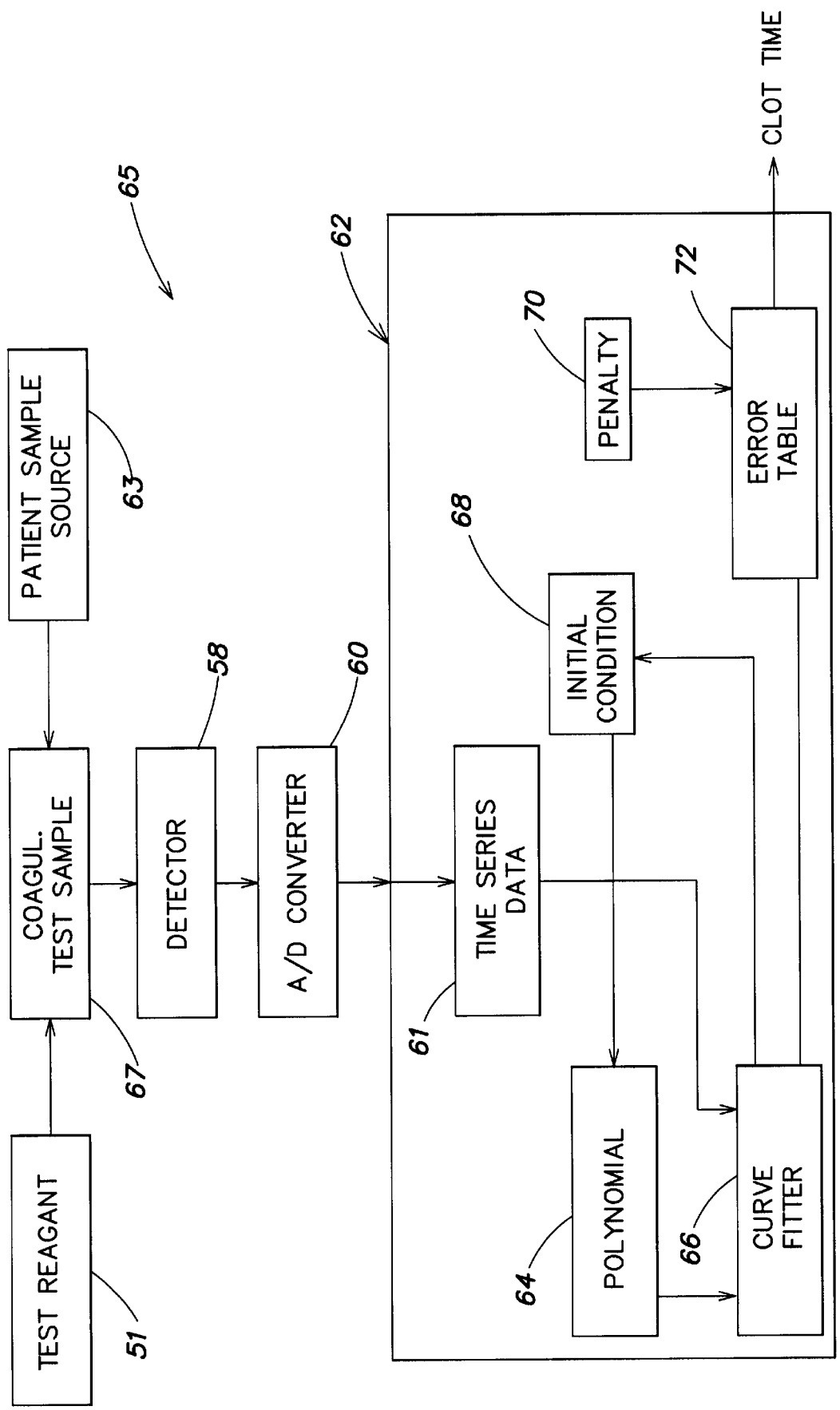
FIG. 7 is a block diagram of a second embodiment of a clot analyzer which uses a polynomial rather than the logistic of FIG. 2B.

Referring now to FIG. 7, a second embodiment of a clot detection system is shown, wherein the second embodiment uses a polynomial algorithm for determining blood clot characteristics. A clot detection system 65 is shown to include a test reagent 51 which is mixed with a patient blood sample source 63 to provide a coagulation test sample 67. As described previously, the test reagent may be any sort of chemical that initiates the clotting process, such as thrombin.

The coagulation test sample 67 is fed to a detector 58 that measures the fibrin polymerization rate by taking optical turbidity measurements over a specified period of time. The time series data from the detector 58 are forwarded to an analog to digital converter 60. The digitized results are forwarded to a processing system 62 and stored as time series data 61. The processing system 62 determines clot time by curve fitting a third-order polynomial 64, which mimics the sigmoidal s-shape of the clotting process (See FIG. 8A), to the time series data at curve fitter 66. After curve fitting the polynomial, the centroid location of the fitted polynomial is evaluated, where the centroid corresponds to the clot time of the time series data.

Figure 8A:
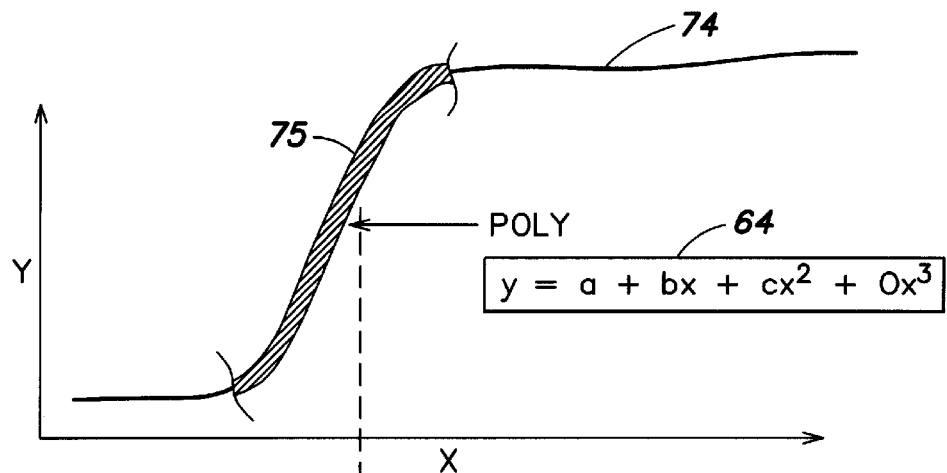
FIGS. 8A–8C are waveforms for use in illustrating the analysis of the polynomial of FIG. 7 for estimating clotting characteristics.
Figure 8B:
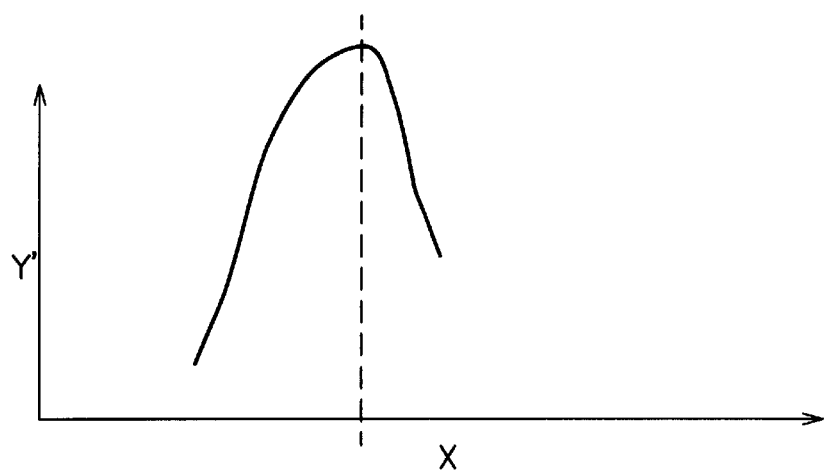
Figure 8C:
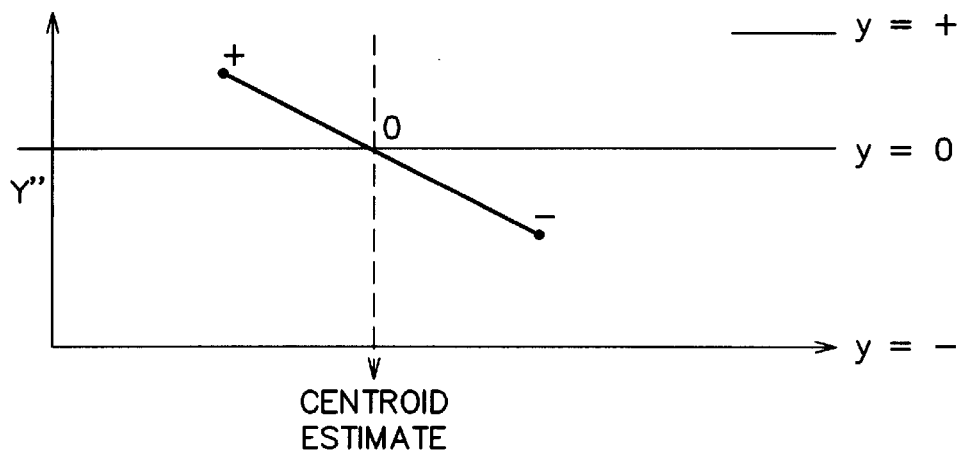

Referring now briefly to FIGS. 8A–8C, example timing diagrams of the third order polynomial and the time series data waveform are shown. In FIG. 8A, the time series waveform is represented by curve 74, with the portion of the third order polynomial to be curve fit to the time series data waveform being indicated in bold as element 75. In FIGS. 8B and 8C, the first derivative of the portion 75 of the polynomial, and the second derivative of the portion 75 of the polynomial are respectively shown.

The polynomial 64 effectively provides a template having a series of optical turbidity measurements for each interval of time, where the shape of the data within the template mimics the sigmoidal s-shape of the clotting process. According to one embodiment of the invention, as described in connection with FIGS. 8A–8C, only a portion of the polynomial curve is fit to the time series waveform to reduce the overall complexity and time required to perform the curve fitting process. Therefore, before performing the curve fitting operation, bounds defining the portion of the polynomial to be fit to the time series data are first selected.

The selection of bounds for analyzing the polynomial may be controlled by the knowledge of the underlying clotting behavior of the sample as described by the logistic portion of Equation (4) and the residual oscillatory component. As described above, the range of solutions for clot times spans the time between the peaks of the second derivative of the logistic and also spans the space of one wavelength of the observed oscillation between the negative peak where the overall optical density begins to increase and the negative peak which occurs just past the peak of the first derivative of the optical density. The highest concentration or density of solutions for clot times occurs just after the positive peak of the observed oscillation, near the first derivative peak of the optical density. Thus, the sample window identified by these data points may be used as initial upper and lower bounds for the curve fit of the third order polynomial. The exact locations of the upper and lower bounds may be determined using the process described above with regard to FIG. 5, where upper and lower bounds are determined for the first derivative of the logistic function.

Referring again to FIG. 7, the bounds over which the polynomial is analyzed are stored at the initial condition register 68. During the curve fit analysis, the differences in optical turbidity values between the polynomial waveform and the time series data waveform are stored as a sum of squares errors in error table 72.

The method of this embodiment of the invention is iterative. During each iteration, the bounded area of the waveform is curve-fit to the optical density signal, and a centroid (identifying the clot signal "c") is generated. Sum of squares differences for the curve fit are stored in the sum of squares error table 72 along with the identified centroid location.

The contents of the sum of squares error table are used to select the probable centroid location of the polynomial, and thus the probable clot time of the time series data. According to one embodiment of the invention, a penalty function 70 is applied to the time series data, where the penalty function 70 may be similar to that described above with regard to the curve fitting of the logistic. Thus, the penalty function 70 incorporates knowledge of how to better weight individual data points to be curve fit, or adjust such things as sum of squares error, to advantageously avoid the chaotic parts of the signal, or vice versa where use of the derived information of the apparent chaotic behavior would result in beneficial information.

After the respective penalties have been applied to each of the entries in the sum of square errors table 72, the sum of square errors are sorted to provide the table entry with the lowest sum of square error. The time associated with the minimum sum of squares errors identifies the centroid of the polynomial function, and hence is analogous to the clot time of the blood sample.

In addition to selecting the centroid of the polynomial (coefficient "c" of the logistic), the polynomial template technique may also be used to provide other initial values of coefficients of the logistic, using the above equations. For example, values within the sum of squares error tables may be used to determine the final coefficients, with solutions related to the sum of square error, the mean solution and the median solution relating to coefficient "f" of the logistic. When numerical methods are used, as described above, the dominant span between the solutions relates to the spacing between peaks described by the part of the logistic equation using coefficients "e", "f", and "g". The highest valued, reasonable solution approximates coefficient "c".

Accordingly, information obtained from the logistic portion of Equation (1) and the residual oscillatory signal may be used to improve the performance of existing polynomial clot detection mechanisms by identifying bounds of the polynomial to be analyzed during the curve fitting process. Intermediate results of the computations are used as initial estimates of the coefficients of Equation (1) representing the clot waveform. In addition, recognizing and appropriately filtering the effects of chaotic interference during curve fitting, allows for higher precision results for clot times to be obtained from existing polynomial template clot detection methods.

Another embodiment of the invention is an improvement upon the process described in Lipscomb, U.S. Pat. No. 4,720,787, incorporated herein by reference. The polynomial curve fitting process described in this example yields estimates for "f" and "c" which may then bootstrap a subsequent curve fit according to Lipscomb.

Translating Coefficients into Blood Characteristics

When the curve fitter indicates a match between the equation model and the time series data waveform, the coefficients of the equation model may be used to determine the factor concentrations of the sample. While there is in some cases a clear relationship between the coefficients from the fitted equations and the factor concentrations, there is not necessarily a one-to-one mapping. For example, although one could convert coefficients b and h to fibrinogen concentration using a calibration curve, and one could use coefficient c as a "clot time" value, there are many dependencies and interactions between the coefficients provided from the curve fitter for defining other components of the patient's blood sample.

Thus, the problem of mapping the output coefficient values to blood components is a multi-variate general linear hypothesis problem that is optimally solved in piece-wise segments. According to one embodiment of the invention, in order to translate the coefficients (FIG. 3, 32) into meaningful output data, either a multi-variate calibration curve or a trained backwards propagation neural network can advantageously be used. When using either multi-variate analysis or neural network analysis, calibration curves for the factors estimates must be made by running calibration assays, as will be described below. However, in order to optimize the operation of the neural network, optimization logic, for example a fuzzy logic case filter (FIG. 3, 34) is provided before the neural network. The optimization logic is used to increase the accuracy and reduce the complexity of the neural network as described below.

Optimization Logic

Optimization logic is described in connection with the embodiment of the invention shown in FIG. 3 to adjust the output coefficients to ensure that the appropriate factor concentrations are provided even in the case of exception conditions. The exceptions are causally understood and recognizable. If the neural network 36 was left to the problem of correlating input data that had not been adjusted to allow for exception conditions, undesired inferences might be made, resulting in incorrect factor concentrations. Thus, the fuzzy logic case filter 34 is provided to modify input information to cope with the causally understood exceptions and thereby minimize the risk of undesired inferences.

For example, consider a case specific to coagulation, where the reaction is starved for thrombin. If it is not recognized at the outset that the reaction is starved for thrombin, a significant over estimation of the fibrinogen concentration would result. Thrombin starvation is indicated by a very high value for coefficient "h" relative to the magnitude of the coefficient "b⇋".

The optimization logic may be implemented in many forms. For example, in the embodiment of FIG. 3, the optimization logic 34 is implemented in the form of fuzzy logic that implements a case filter before the neural network 36. Fuzzy logic is basically a programming philosophy that deals with imprecise numbers as opposed to exact values. More specifically, fuzzy logic deals with the implications and outcome of components having a value within a certain range. Fuzzy logic may be implemented using software program codes or instructions and case conditions to correct for certain exception conditions as described above.

Although the use of optimization logic 34 improves the accuracy of some embodiments of the present invention, particularly in instances where exception conditions exist, it is not a requirement of the present invention.

Calibrating an Inference of Blood Characteristics from the Coefficients

The invention may be embodied in a system which infers blood characteristics from the coefficients formed by one of the above described systems. For example, blood characteristics can be inferred from coefficients of the model presented above using logistics.

These methods for predicting, estimating, chemical concentrations or "percent activities" as they are often labeled require that some sort of matrix of tests be conducted with the intended reagents and a set of calibration plasma samples. For traditional factor assays of one clotting factor one typically runs a series of dilutions of a known plasma, called a control plasma. This control plasma typically is a commercially prepared pre-assayed plasma. It is known in addition that if one pools from a number of healthy persons plasma obtained from this number of individuals one can create a pooled plasma which can be described as 100% in factor activity. The concentrations of each of the individual chemicals will be close to known mean values in the general population. One basically is creating in chemicals an average value. Control plasmas lacking a specific known chemical can either be synthetically manufactured or obtained from pools of individuals who are known to have a genetic deficiency. Thus one can produce a data set from a particular instrument, lot of reagent, and dilution series or pre-assayed plasma of measured "clot time" versus concentration or "percent activity". With this data set one can create a calibration curve, either on graph paper or in the form of a computer generated fitted equation from which unknown patient samples measured in "clot time" can be converted mathematically to factor concentration or "percent activity".

Where one would likely perform a similar method only as a multidimensional problem of many unknown clotting factors or other related chemicals one would need to establish a multidimensional calibration matrix of measured parameters such as "clot time" and the curve fit coefficients of the logistic of Equation (1), versus an assortment of known mixtures of various factor concentrations of plasmas. Instead of a two dimensional problem of mapping one chemical concentration to the directly measured parameter it becomes an N-dimensional problem of mapping multiple directly measured parameters to multiple variations of multiple chemical concentrations. The calibration mapping is represented by an N-dimensional hypercube.

There is a need for a practical, viable, way to reliably achieve calibration, (called "training" when one is using neural networks), for coagulation instruments. One approach, which would both minimize the effort required of a user, as well as create a salable product, would be for the reagent manufacturer to pre-calibrate specific instrument models to specific lots of reagent. The reagent manufacturer then does the work once for a lot of reagent rather than requiring each individual user to perform the work on their own. The calibration information could be supplied in various formats such as on a floppy disk, a CD ROM, a credit card like strip, embedded in a "dongle"-like semiconductor chip such as is used for software license keys, on a tape cassette, through the Internet or a modem download, or other similar means. Access to this calibration information could be included with the reagent product or provided as a separate product.

An alternative means would be for the reagent manufacturer to provide a "calibration kit" which would contain a specific assortment of pre-assayed plasmas of known concentrations for the necessary calibration points. The pre-assayed plasmas could be, but not necessarily, be packaged in racks suitable for directly loading into automated sampling systems of the target instrument to minimize handling operations. The pre-assayed plasmas also could be pre-labeled for automated reading of the necessary calibration information by the instrument by such means as optical bar codes or magnetic stripes.

A hybrid technique may alternatively be used when the reagent manufacturer pre-calibration approach was slightly imprecise due to slight differences between individual instruments (such as differences in individual temperature control or fluidics). In such a case the pre-calibration approach could provide the overall pattern of the calibration mapping. A limited number of specific calibration plasmas could then also be provided to the user and run by the user on the user's specific instrument to obtain the information needed to tighten up the specific calibration.

It should be noted that no matter how the calibration method is managed there is also a regulatory imposed requirement on users to prove calibration and quality control. There are an assortment of laws, regulations, and standards requiring proof of quality control.

Users need to run both calibration curves and controls. Controls are plasmas that are used to check performance. One ought to get a specific result from each of the specific controls. When either of the neural network based or multi-variate analysis based coagulation chemistry estimation schemes was implemented, the reagent manufacture would need to provide at least a minimum number of control plasmas in a form similar to that suggested for the alternative calibration method to enable the user to verify calibration and also to train the neural network.

The neural network (FIG. 3, 36) is essentially a multi-variate general linear hypothesis mechanism that can cope with non-linearity of relationships between the output coefficients (FIG. 3, 32) and the ultimate factor concentration results (FIG. 3, 38). A neural network is an inference machine that provides an output conclusion based on a number of weighted inputs. The neural network may either define a linear relationship between the coefficients (FIG. 3, 32) and ultimate factor results (FIG. 3, 38), or alternatively may define other, non-linear relationships between the two. For example, the neural network may use a sigmoidal function to define a curvilinear relationships between the coefficients and factor results. The neural network is comprised of a number of interconnected layers of nodes, each of which communicate with other nodes in the network when stimulated to a predetermined activation level by coupled inputs. Both the connections between the nodes and the activation levels of each of the nodes are defined according to the function emulated by the neural network. The neural network may use either one layer of neurons to capture the curvilinear relationship, or alternatively may use several layers of neurons to provide piece-wise curvilinear segments.

Figure 9:
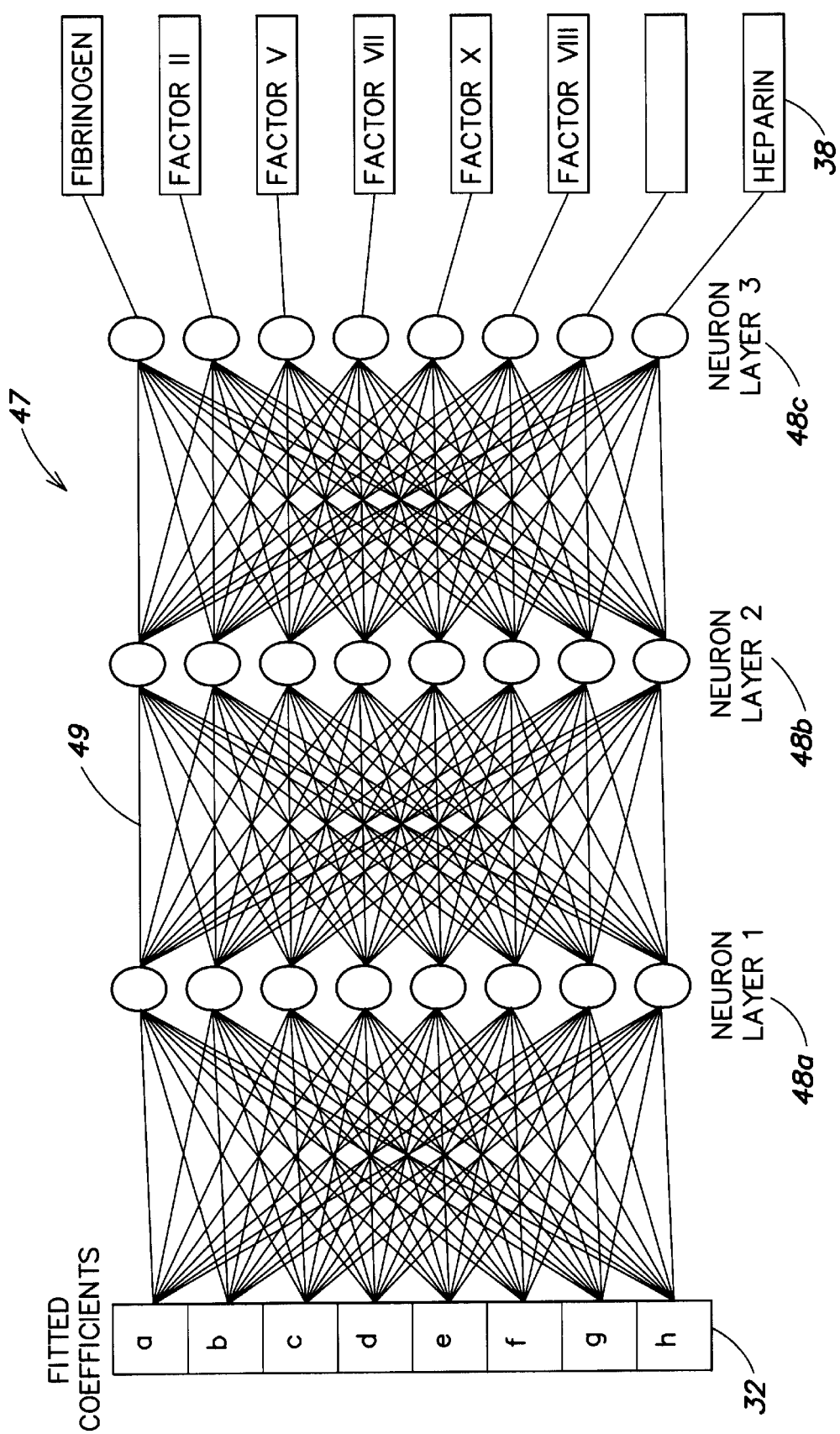
FIG. 9 is a block diagram of one embodiment of a neural network for use in the clot analysis system of FIG. 1.

Referring now to FIG. 9, an example structure of a neural network 47 for providing factor results 38 based on input coefficients 32 is shown including several layers of neurons 48a, 48b, and 48c. Each neuron of each layer is coupled to one or more neurons in the next layer via neural nets (shown as signal lines 49 in FIG. 8). Each neuron receives a number of weighted inputs. The weighted inputs values may fall anywhere in the range from 100% on (1) to off (0). Depending upon the values of the inputs at the neuron, and an equation at the neuron, the neuron propagates a signal having a certain weight to one or more neighboring neurons in the network.

For example, using a sigmoidal function to define the operation of the neural network of FIG. 9, a given node in the neural network may be defined by Equation (9) shown below:

$$Output(A[i]) = \frac{k_1}{1 + \frac{\exp\left(-k_2 + \sum_{i=0}^{n} A[i]W[i]\right)}{k_3}} \quad (9)$$

where exp indicates the exponential function, A[i] is an array of n input values for the neuron and the coefficient $k_1$ determines the amplitude of the output of the neuron. The coefficient $k_3$ is a scale factor determining the degree to which a change in the input is reflected at the output. W[i] is an array of input weights, which correspond to slopes in multi-variate linear regression. The process of selecting values for the W[i] array, which in turn determines the input values that will activate a neuron, is called "training" when solving a problem using neural networks.

Although three layers 48a, 48b and 48c of neural networks are shown in FIG. 9, it should be understood that the structure illustrated is merely an exemplary implementation of a neural network. Thus, there may be greater or fewer layers, with each layer including more or fewer neurons interconnected in a variety of ways depending upon the chemical analysis and factors that are being evaluated.

Accordingly, a method and apparatus for analyzing blood factors has been shown to use a model equation which closely models the chemical characteristics of the clotting process. Initial coefficient values for the model equation may be determined either directly from the first derivative of the logistic or by detrending the time series waveform to extract an oscillatory component representative of the fibrin folding characteristic of the clot waveform. Using these coefficients, and advantageously using fuzzy front end logic, an inference engine may be provided for determining factor concentrations of the blood sample.

Clot Simulation Method and Apparatus

During development of clot detection instruments, whether these instruments are mechanically, acoustically, or optically based, there is a need for generating clot-like signals for the purpose of design and testing both the hardware and the algorithms used during the engineering and manufacturing of the clot detection systems. There is also a need to generate similar systems for the verification and functionality of the clot detection systems when they reach the ultimate users. Because medical facilities are controlled by various government regulations that require certain levels of quality during their detection phases, it is thus desirable to verify and test the performance of instrument using repeatable test inputs before it is used in an actual application.

Typical prior art methods that were used to generate clot-like signals for design and test of the clot detection systems used either a hardware, electronic based signal generator, that mimicked a simple inverse operation of the signal analysis of the blood clot, or alternatively used a digitally recorded clotting signal that was played back through a digital to analog converter. The problem with using a signal generator was that the detection system merely mimicked the signal that was generated and not a realistic clot. The digitally recorded method thus provided better results than the signal generation technique. However, one drawback of the digitally recorded clotting signal technique was that the recorded signal represented only one clotting event under one set of conditions. Therefore, the signal played back sometimes required mathematical modification in order to fully test all of the characteristics and various clotting type signals caused by different reactants.

Therefore, a need exists to be able to repetitively sequence a large number of similarly appearing clotting signals each having slight variations and statistically random noise, for the purposes of verifying clot detection. The need similarly exists for the design of the detection electronics, photo-optical detector, pre-amplifier, and digitizing components.

Using Equation (1), as described above, close replicas of clotting signals may be provided for simulation purposes since the equation model closely replicates the behavior of blood coagulation under variable conditions. The equation model may be used to produce realistic signals that can be varied at will to represent the effects of varying chemical conditions, such as fibrinogen concentrations, on the clot time. In addition, the equation model can be modified to mathematically mimic, in a realistic manner, background noise so that things such as bubbles from reagent injections, photo diode noise and background hissing can be added to the simulated clotting signal. According to one embodiment of the invention, the noise portion of the overall mathematical model may be constructed using a statistically based random noise generator for the purpose of improving the design of clot detection instruments.

One equation having fixed coefficients models only one particular clotting event. However, when the coefficients are varied the equation is general enough to describe a class of events and group of clotting events that were curve fitted, each being slightly different from the other in a known and controlled fashion. Accordingly, one can use the equation with varied coefficients, where the variations represent different initial conditions, to provide useful simulated clotting signals.

Therefore, if a series of clotting events, such as PT saline dilution of a control, or a PT factor II dilution were curve fit, then one would be able to build a model that could mimic this sequence of clotting activities. The equation model thus is constructed by curve fitting the coefficients provided by an original curve fit to the variable or variables being modified, such as the dilution ratio. The second curve fit acts as a map of the coefficients over the input variable space.

Figure 10:
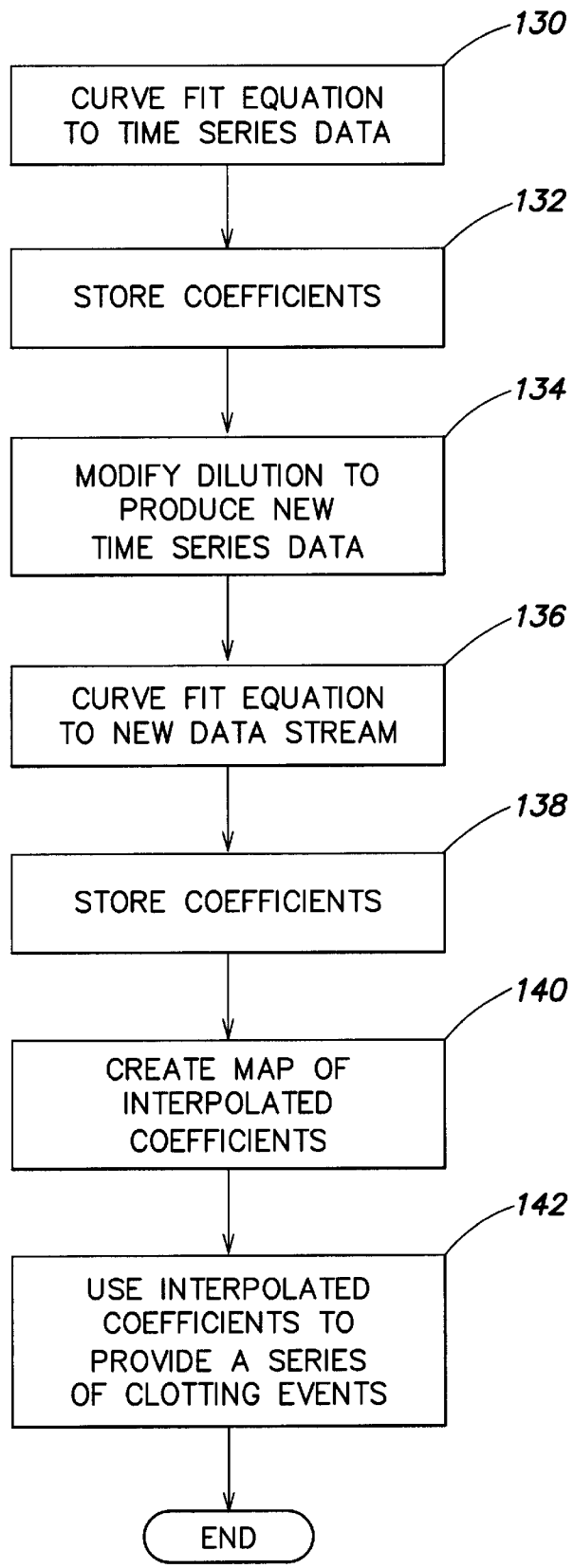
FIG. 10 is a flow diagram illustrating a process for using the non-linear function of the embodiment of FIG. 1 for testing clot analysis instrumentation.

Referring now to FIG. 10, a flow diagram that illustrates the method of providing an equation model for use in simulating clots is shown. At step 130, the equation is curve fit to a baseline time series data waveform obtained for a reagent-plasma combination of interest. At step 132, the coefficients of the first curve fit are stored. At step 134, the reagent-plasma combination of interest is modified, and a new set of time series data is provided for a simulated clot. At step 136, a second curve fit is performed to identify the change in coefficients as a result of the modification. At step 138, the modified coefficients are stored. At step 140, a sequence of interpolated coefficients, representing different dilution ratios is provided using the relative differences provided by the first and second curve fit operations. At step 142, the coefficients are then used in the clot generating equation model to produce the time series simulation of the clotting event.

Accordingly, a set of coefficients may be provided that represent different types of clotting events. In operation, the different equation models may then be provided to simulate different types of clotting characteristics and events for testing a clot detection system.

A Practical System

Figure 11:
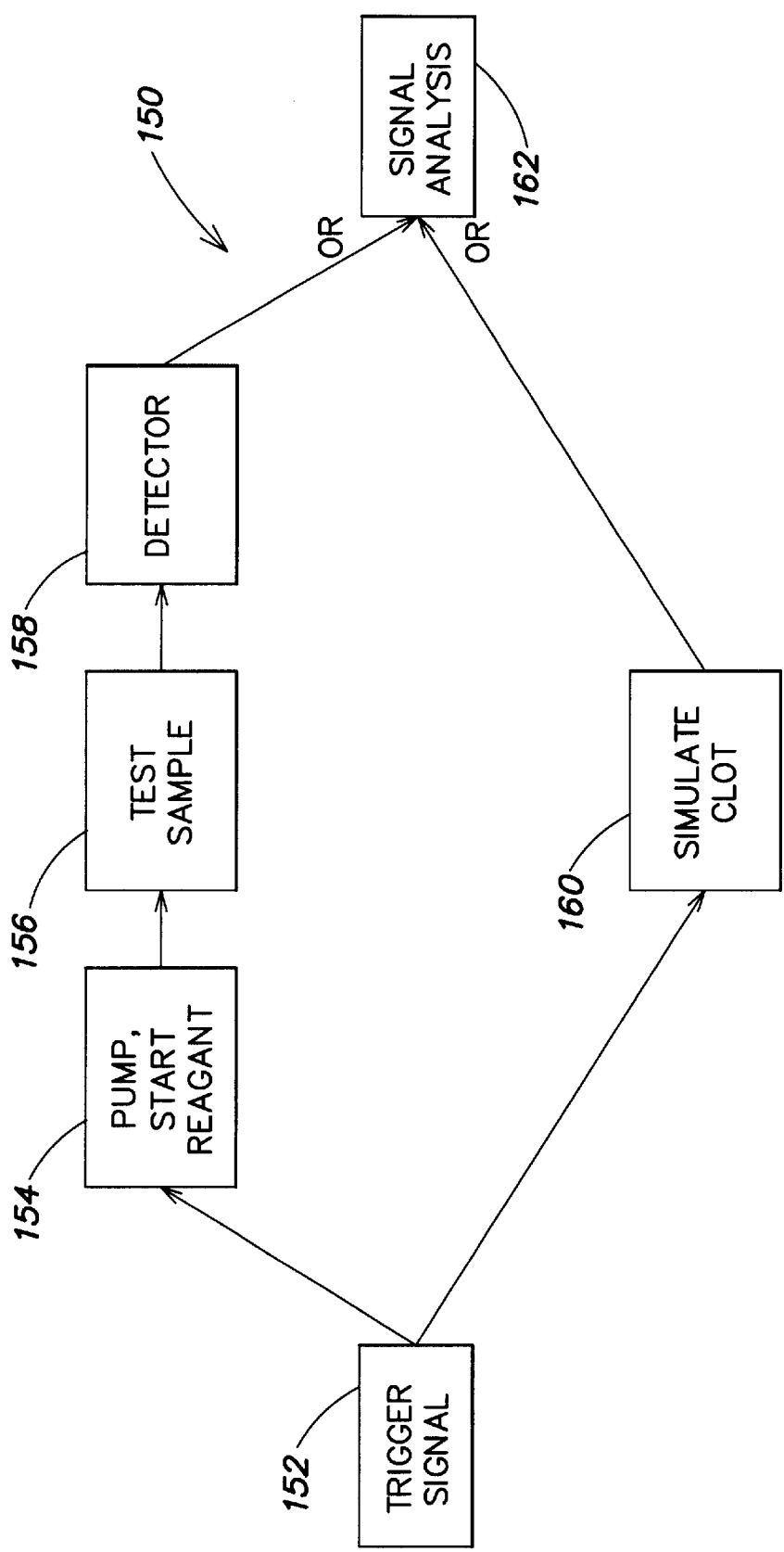
FIG. 11 is a block diagram of a system incorporating both clot analysis and clot instrument verification tools.

Referring now to FIG. 11, a block diagram of a clot analysis system incorporating both a means for doing clot analysis and a means for testing the equipment analysis is provided. In FIG. 11, an upper path 150 illustrates the operative flow when the instrument is performing clot analysis. Thus, a trigger signal 152 is sent by a host computer to initiate the analysis of patient sample. The trigger signal 152 is forwarded to a start reagent pump 154 that delivers the reagent to cause the test sample 156 to coagulate. The level of fibrin polymerization is analyzed by the detector 158 and the clot results are forwarded to signal analysis means 162. The signal analysis means may use either the equation model method of clot analysis described with reference to FIG. 3, or the polynomial method described with reference to FIG. 7, or may use another type of clot detection system available in the art.

The lower path illustrates the mechanism used to simulate a clot for the purpose of testing the analysis means 162. At the start of the test, the computer issues the trigger signal 152 which is forwarded to the equation model simulator 160. The trigger signal may include, for example, information as to what type of clot should be simulated, i.e., what clotting factor levels and noise signals are desired to test the signal analysis means 162. As described above, the equation model simulator includes different coefficients for each of a plurality of types of clotting events to be simulated. Accordingly, a type of clotting event is selected by the computer system and forwarded with trigger signal 152 to the equation model 160, a simulated clot signal having the desired characteristics is provided to the signal analysis means 162. Accordingly, a new method has been provided for testing the operational abilities of a clot detection system that does not require the use of memory intensive digital recordings or imperfect inverse analysis algorithms.

Having described illustrative embodiments of the invention, it should be understood that while the invention has been particularly shown and described above with reference to these embodiments, various modifications in form and detail may be made therein by one skilled in the art while still remaining within the spirit and the scope of the invention which is to be determined by properly construing the following claims.

What is claimed is:

1. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing a relationship between initial concentrations of plural blood factors and fibrin polymerization at least in part by one non-linear function having a plurality of coefficients which are related to the initial concentration of plural blood factors through multivariate backward correlation; and curve fitting the model to the first signal to produce an output representing values of the plurality of coefficients causing the model to conform to the first signal, wherein the values of the plurality of coefficients are used to identify physical parameters of the blood sample.

2. The method for determining the physical characteristics of a blood sample according to claim 1, further comprising the step of transforming the values of the plurality of coefficients to provide derived physical parameters of the blood sample.

3. The method for determining the physical characteristics of a blood sample of claim 1 wherein the physical parameters include clot time.

4. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation; and curve fitting the model to the first signal to produce an output representing values of the plurality of coefficients causing the model to conform to the first signal, wherein the values of the plurality of coefficients are used to identify physical parameters of the blood sample;

wherein the physical parameters include clot time; and wherein the clot time substantially correlates with one of the plurality of coefficients representing a centroid location of the non-linear function.

5. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

wherein the physical parameters include clot time; and wherein the clot time substantially correlates to a centroid location of the second derivative of the non-linear function.

6. The method for determining the physical characteristics of a blood sample according to claim 1 wherein the first signal is an optical density signal.

7. The method for determining the physical characteristics of a blood sample according to claim 1, wherein the first signal is a turbidity signal.

8. The method for determining the physical characteristics of a blood sample of claim 1, wherein the step of curve fitting further comprises the step of:

estimating initial values of the plurality of coefficients of the non-linear function.

9. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

wherein curve fitting further includes estimating initial values of the plurality of coefficients of the non-linear function; and wherein estimating initial values determines the values of the plurality of coefficients responsive to characteristics of a low-level oscillatory component of the first signal.

10. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

wherein curve fitting further includes estimating initial values of the plurality of coefficients of the non-linear function; and wherein estimating initial values determines the values of the plurality of coefficients responsive to characteristics of the first derivative and second derivative of the first signal.

11. The method for determining the physical characteristics of a blood sample of claim 10, wherein the initial values are derived responsive to located vanishing points of the first derivative of the first signal.

12. A method for determining the physical characteristics of a blood sample, comprising:
   producing a first signal indicative of a measurement of fibrin polymerization of a blood sample over a period of time;
   providing an analytical model of fibrin polymerization of the blood sample over a period of time, the model representing at least in part by a non-linear function having a plurality of coefficients which are related to the initial concentration of plural blood factors through multi-variate backward correlation;
   curve fitting the model to the first signal to produce an output representing values of the plurality of coefficients causing the model to conform to the first signal, wherein the values of the plurality of coefficients are used to identify physical parameters of the blood sample;
   wherein curve fitting further includes estimating initial values of the plurality of coefficients of the non-linear function; and
   wherein the non-linear function is a polynomial function, and wherein estimating initial values of the coefficients derives the coefficients responsive to characteristics of a third derivative of the polynomial function.

13. The method for determining the physical characteristics of a blood sample according to claim 12, wherein the step of estimating initial values further comprises the steps of:
   searching for vanishing points of the third derivative of the polynomial function to identify bounds of the third derivative of the polynomial function for analysis;
   iteratively modifying the bounds of the polynomial to curve fit to the first signal to identify a plurality of potential centroid locations of the polynomial, wherein each of the plurality of identified centroid locations are stored in a table with an associated chi square error of the curve fit;
   modifying the error values in the table by applying a penalty value to each of the error values in the table responsive to chaotic characteristics of the first signal; and
   selecting one of the centroid locations of the plurality of centroid locations as an initial estimated coefficient responsive to the modified error value associated with the selected centroid location in the table.

14. The method for determining the physical characteristics of a blood sample according to claim 13, wherein the step of searching for vanishing points of the third derivative of the polynomial is controlled responsive to information from the non-linear function.

15. The method for determining the physical characteristics of a blood sample of claim 1 wherein the physical parameters are selected from a group consisting essentially of initial concentration of blood clotting factors in the blood sample, anti-coagulants, FDP, d-dimer, selected chemistry anti-coagulants and antibodies.

16. A method for determining the physical characteristics of a blood sample, comprising:
   producing a first signal indicative of a measurement of fibrin polymerization of a blood sample over a period of time;
   providing an analytical model of fibrin polymerization of the blood sample over a period of time, the model representing at least in part by a non-linear function having a plurality of coefficients which are related to the initial concentration of plural blood factors through multi-variate backward correlation; and
   curve fitting the model to the first signal to produce an output representing values of the plurality of coefficients causing the model to conform to the first signal, wherein the values of the plurality of coefficients are used to identify physical parameters of the blood sample;
   wherein the non-linear function is $$a + \frac{(b+ht)}{1+\left(\frac{t}{c}\right)^d} + \frac{2\left(eg^2\left(\frac{t}{f}\right)\right)^{(-2-2g)}}{\left(f^2\left(1+\left(\frac{t}{f}\right)^g\right)\right)^3} - \frac{eg(-1+g)\left(\frac{t}{f}\right)^{(-2+g)}}{\left(f_2\left(1+\left(\frac{t}{f}\right)^g\right)\right)^2},$$

where a, b c, d, e, f and g represent the plurality of coefficients and t represents time.

17. The method according to claim 1 wherein the first signal is produced by an optical nephelometer, and the density signal indicates a turbidity of the blood sample.

18. The method according to claim 1 wherein the first signal is produced by a Fiberometer.

19. The method for determining the physical characteristics of a blood sample according to claim 3, wherein the step of transforming further comprises the steps of:
   modifying the values of the plurality of coefficients to correct exception conditions; and
   translating the modified values of the plurality of coefficients to the derived physical parameters of the blood sample according to a defined operative function.

20. The method for determining the physical characteristics of a blood sample according to claim 19, wherein the means for translating the modified values comprises a multi-variate general linear hypothesis mechanism.

21. A method for determining the physical characteristics of a blood sample, comprising:
   producing a first signal indicative of a measurement of fibrin polymerization of a blood sample over a period of time;
   providing an analytical model of fibrin polymerization of the blood sample over a period of time, the model representing at least in part by a non-linear function having a plurality of coefficients which are related to the initial concentration of plural blood factors through multi-variate backward correlation;
   curve fitting the model to the first signal to produce an output representing values of the plurality of coefficients causing the model to conform to the first signal, wherein the values of the plurality of coefficients are used to identify physical parameters of the blood sample;
   transforming the values of the plurality of coefficients to provide derived physical parameters of the blood sample;
   wherein transforming further includes:
      modifying the values of the plurality of coefficients to correct exception conditions;
      translating the modified values of the plurality of coefficients to the derived physical parameters of the blood sample according to a defined operative function; and
      wherein translating the modified values is performed using a neural network.

22. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

transforming the values of the plurality of coefficients to provide derived physical parameters of the blood sample;

wherein transforming further includes:
  modifying the values of the plurality of coefficients to correct exception conditions;
  translating the modified values of the plurality of coefficients to the derived physical parameters of the blood sample according to a defined operative function; and
  wherein translating the modified values optimizing is performed using fuzzy logic.

23. A method for determining the physical characteristics of a blood sample, comprising the steps of:

producing a first signal indicative of a measurement of fibrin polymerization of a blood sample over a period of time; and extracting a low level oscillation signal from the optical density signal, wherein the low level oscillation signal is used to determine the characteristics of the blood sample.

24. The method for determining the physical characteristics of a blood sample according to claim 23, further comprising the step of determining a clot time of the blood sample responsive to the low level oscillation signal.

25. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

extracting a low level oscillation signal from the first signal, wherein the low level oscillation signal is used to determine the characteristics of the blood sample; and determining a clot time of the blood sample responsive to the low level oscillation signal;

wherein determining the clot time of the blood sample includes analyzing the frequency of the low level oscillation signal using an analysis method selected from the group consisting of Fourier analysis, fast Fourier transform analysis, wavelet analysis, peak and minimum search analysis and phase locked analysis.

26. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

extracting a low level oscillation signal from the first signal, wherein the low level oscillation signal is used to determine the characteristics of the blood sample;

determining, responsive to the low level oscillation, characteristics of the blood sample; and correcting characteristic estimations of the blood sample responsive to frequency of the low level oscillation.

27. The method for determining the physical characteristics of a blood sample according to claim 26, wherein the characteristic estimations include fibrinogen estimations.

28. The method for determining the physical characteristics of a blood sample according to claim 26, wherein the step of correcting characteristic estimations includes the step of analyzing the frequency of the low level oscillation signal using an analysis method selected from the group consisting of Fourier analysis, fast Fourier transform analysis, moving fast Fourier transform window analysis, wavelet analysis and peak and minimum search analysis.

29. The method for determining the physical characteristics of a blood sample according to claim 26, wherein the step of correcting characteristic estimations includes the step of inferring relationships between the frequency of the low level oscillation and one or more characteristics to be corrected.

30. The method for determining the physical characteristics of a blood sample according to claim 29, wherein the step of inferring relationships is performed by a trained neural network.

31. The method for determining the physical characteristics of a blood sample according to claim 29, wherein the step of inferring relationships is performed using fuzzy logic.

32. The method for determining the physical characteristics of a blood sample according to claim 29, wherein the step of inferring relationships is performed using one or more multi-variate calibration curves.

33. The method for determining the physical characteristics of a blood sample according to claim 26, wherein the characteristics are selected from a group consisting essentially of fibrin strand mass length ratios, reactant concentrations and abnormalities and kinetic reaction rates of the blood sample.

34. The method for determining the physical characteristics of a blood sample according to claim 23, further comprising the steps of:

providing a mathematical model of the measurement of fibrin polymerization of the blood sample over the given period of time, the mathematical model comprising a plurality of coefficients, wherein the mathematical model is curve fit to the first signal provided by the detector and wherein values of the coefficients may be used to identify physical characteristics of the blood sample; and determining, responsive to the low level oscillation signal, initial estimates of the coefficients of the mathematical model for the curve fit.

35. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

extracting a low level oscillation signal from the first signal, wherein the low level oscillation signal is used to determine the characteristics of the blood sample;

providing a mathematical model of the measurement of fibrin polymerization of the blood sample over the given period of time, the mathematical model comprising a plurality of coefficients, wherein the mathematical model is curve fit to the first signal provided by the detector and wherein values of the coefficients may be used to identify physical characteristics of the blood sample; and determining, responsive to the low level oscillation signal, initial estimates of the coefficients of the mathematical model for the curve fit;

wherein determining the clot time of the initial coefficients includes analyzing the frequency of the low level oscillation signal using an analysis method selected from the group consisting of Fourier analysis, fast Fourier transform analysis, wavelet analysis, peak and minimum search analysis and phase locked loop analysis.

36. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample;

extracting a low level oscillation signal from the first signal, wherein the low level oscillation signal is used to determine the characteristics of the blood sample;

providing a mathematical model of the measurement of fibrin polymerization of the blood sample over the given period of time, the mathematical model comprising a plurality of coefficients, wherein the mathematical model is curve fit to the first signal provided by the detector and wherein values of the coefficients may be used to identify physical characteristics of the blood sample; and determining, responsive to the low level oscillation signal, initial estimates of the coefficients of the mathematical model for the curve fit;

wherein the mathematical model is represented by the below equation:

$$a + \frac{(b+ht)}{1+\left(\frac{t}{c}\right)^d} + \frac{2\left(eg^2\left(\frac{t}{f}\right)\right)^{(-2-2g)}}{\left(f^2\left(1+\left(\frac{t}{f}\right)^g\right)\right)^3} - \frac{eg(-1+g)\left(\frac{t}{f}\right)^{(-2+g)}}{\left(f_2\left(1+\left(\frac{t}{f}\right)^g\right)\right)^2},$$

where a, b c, d, e, f and g represent the plurality of coefficients and t represents time.

37. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample; and extracting a low level oscillation signal from the first signal, wherein the low level oscillation signal is used to determine the characteristics of the blood sample;

wherein extracting the low level oscillation signal is performed using residuals analysis of the first signal.

38. A method for determining the physical characteristics of a blood sample, comprising:

producing a first signal indicative of a measurement of fibrin polymerization of a blood sample over a period of time;

providing an analytical model of fibrin polymerization of the blood sample over a period of time, the model representing at least in part by a non-linear function having a plurality of coefficients which are related to the initial concentration of plural blood factors through multi-variate backward correlation;

curve fitting the model to the first signal to produce an output representing values of the plurality of coefficients causing the model to conform to the first signal, wherein the values of the plurality of coefficients are used to identify physical parameters of the blood sample; and extracting a low level oscillation signal from the first signal, wherein the low level oscillation signal is used to determine the characteristics of the blood sample;

wherein extracting the low level oscillation signal performs a repetitive polynomial detrending of the first signal to retrieve the low level oscillation signal.

39. The method for determining the physical characteristics of a blood sample according to claim 23 further comprising the step of:
filtering the first signal to reduce a number of the first signals that are transferred to the curve fitter.

40. A method for determining the physical characteristics of a blood sample, comprising:
producing a first signal indicative of a measurement of fibrin polymerization of a blood sample over a period of time;
providing an analytical model of fibrin polymerization of the blood sample over a period of time, the model representing at least in part by a non-linear function having a plurality of coefficients which are related to the initial concentration of plural blood factors through multi-variate backward correlation;
curve fitting the model to the first signal to produce an output representing values of the plurality of coefficients causing the model to conform to the first signal, wherein the values of the plurality of coefficients are used to identify physical parameters of the blood sample;
extracting a low level oscillation signal from the first signal, wherein the low level oscillation signal is used to determine the characteristics of the blood sample; and
identifying blood samples having weak clotting characteristics, wherein identifying includes
polynomial detrending which removes external noise from the first signal by adjusting values of a portion the accumulated data signals; and
interpolating which smoothes the interface between said adjusted portion of said accumulated data signals and remaining accumulated data signals.

41. A method for determining the physical characteristics of a blood sample, comprising:
producing a first signal indicative of a measurement of fibrin polymerization of a blood sample over a period of time;
providing an analytical model of fibrin polymerization of the blood sample over a period of time, the model representing at least in part by a non-linear function having a plurality of coefficients which are related to the initial concentration of plural blood factors through multi-variate backward correlation;
curve fitting the model to the first signal to produce an output representing values of the plurality of coefficients causing the model to conform to the first signal, wherein the values of the plurality of coefficients are used to identify physical parameters of the blood sample;
storing, for each manipulation of the bounds of the polynomial model, a difference between the bounded waveform and the first signal, the table also for storing a centroid location of the associated model; and
selecting the bounds of the polynomial model responsive to a non-linear logistic model of the first signal.

42. The method for determining the clotting characteristics of a blood sample of claim 41, further comprising the step of:
selecting one of the centroid locations of one of the plurality of models as a clot time of the blood sample responsive to the corresponding difference signal of the model.

43. The method for determining the clotting characteristics of a blood sample according to claim 41, further comprising the steps of:
storing, in a penalty table, a plurality of penalties, each penalty corresponding to the unit of time of one of the first signals and representing potential chaotic behavior of the first signal at the unit of time; and
applying the plurality of penalties to the differences in the table, wherein one of the plurality of penalties is selected for applying to one of the stored differences responsive to the centroid location of the model.

* * * * *

UNITED STATES PATENT AND TRADEMARK OFFICE
CERTIFICATE OF CORRECTION

PATENT NO. : 6,524,861 B1
DATED : February 25, 2003
INVENTOR(S) : Anderson

It is certified that error appears in the above-identified patent and that said Letters Patent is hereby corrected as shown below:

Column 13,
Line 44, please insert -- function -- after "such".

Column 27,
Lines 21-22 and 26-27, please delete "for determining the physical characteristics of a blood sample".
Line 23, please delete "the step of".

Column 28,
Lines 5-6, 8-9, 11-12 and 63-64, please delete "for determining the physical characteristics of a blood sample".
Lines 12 and 13, please delete "the step of".

Column 29,
Lines 25-26, 46-47 and 51-52please delete "for determining the physical characteristics of a blood sample".
Lines 26-27, 27-28 and 47-48, please delete "the step of".

Column 30,
Lines 23-24 and 31-32, please delete "for determining the physical characteristics of a blood sample".
Line 24, please change "3" to -- 2 --.
Lines 24-25, please delete "the step of".
Line 25, please delete "the steps of".
Lines 32-33, please delete "the means for".
Line 33, please replace "comprises"with -- is performed using --.

Column 31,
Lines 28-29, please replace "A method for determining the physical characteristics of a blood sample, comprising the steps of:" with -- The method of claim 1, further comprising: --.
Lines 30-32, please delete "producing a first signal indicative of a measurement of fibrin polymerization of a blood sample over a period of time; and".
Lines 33-34, please replace "optical density" with -- first --.
Lines 37-38, please delete "for determining the physical characteristics of a blood sample"
Line 39, please delete "the step of".

UNITED STATES PATENT AND TRADEMARK OFFICE
CERTIFICATE OF CORRECTION

PATENT NO.    : 6,524,861 B1
DATED         : February 25, 2003
INVENTOR(S)   : Anderson It is certified that error appears in the above-identified patent and that said Letters Patent is hereby corrected as shown below:

<u>Column 32,</u>
Lines 29-30, please delete "determining the physical characteristics of a blood sample"
Lines 32-33, 40-41, 46-47, 50-51, 54-55, 58-59 and 64-65, please delete "for determining the physical characteristics of a blood sample".
Lines 33-34, 34-35, 41-42, 42-43, 47-48, 51-52, 55-56 and 66, please delete "the step of".

<u>Column 35,</u>
Lines 4-5, please delete "for determining the physical characteristics of a blood sample"
Line 6, please delete "the step of".

<u>Column 36,</u>
Lines 22-23 and 29-30, please delete "for determining the physical characteristics of a blood sample".
Lines 23-24 and 31, please delete "the step of".

Signed and Sealed this

Second Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,524,861 B1
DATED        : February 25, 2003
INVENTOR(S)  : Anderson It is certified that error appears in the above-identified patent and that said Letters Patent is hereby corrected as shown below:

Drawings,
Sheet 11, Fig. 8A, in the box denoted by reference number 64, please change "$Ox^3$" to -- $dx^3$ --.

Signed and Sealed this

Ninth Day of December, 2003

JAMES E. ROGAN
*Director of the United States Patent and Trademark Office*